(12) United States Patent
Chou

(10) Patent No.: US 10,231,806 B2
(45) Date of Patent: Mar. 19, 2019

(54) ALIGNING APPARATUS USED IN FABRICATING DENTAL PROSTHESES

(71) Applicant: Jang-Ching Chou, Overland Park, KS (US)

(72) Inventor: Jang-Ching Chou, Overland Park, KS (US)

( * ) Notice: Subject to any disclaimer, the term of this patent is extended or adjusted under 35 U.S.C. 154(b) by 0 days.

(21) Appl. No.: 15/781,728

(22) PCT Filed: Mar. 13, 2018

(86) PCT No.: PCT/US2018/022243
§ 371 (c)(1),
(2) Date: Jun. 6, 2018

(87) PCT Pub. No.: WO2018/222243
PCT Pub. Date: Dec. 6, 2018

(65) Prior Publication Data
US 2018/0368952 A1    Dec. 27, 2018

Related U.S. Application Data

(60) Provisional application No. 62/512,075, filed on May 29, 2017.

(51) Int. Cl.
*A61C 9/00*        (2006.01)
*A61C 13/097*    (2006.01)
(Continued)

(52) U.S. Cl.
CPC .......... *A61C 9/0006* (2013.01); *A61C 13/097* (2013.01); *A61C 13/0004* (2013.01); *A61C 13/34* (2013.01); *A61C 19/05* (2013.01)

(58) Field of Classification Search
CPC ......... A61C 9/0006; A61C 9/00; A61C 19/05; A61C 19/04; A61C 13/00
See application file for complete search history.

(56) References Cited

U.S. PATENT DOCUMENTS 1,714,185 A    5/1929    Morgan
1,734,398 A    11/1929   Phillips
(Continued)

OTHER PUBLICATIONS

ASHMARIP, Prior Art Search Report, Jaw Registration Device and Method of Fabrication of Dental Prostheses, Case: JCC-2017-01, AshmarIP Docket: PASR-JCC-2017-01, Mar. 4, 2017, 71 pp, Newport Beach, CA 92658.

(Continued)

*Primary Examiner* — Ralph A Lewis
(74) *Attorney, Agent, or Firm* — Louis Ventre, Jr.

(57) ABSTRACT

A tray appliance system is usable for obtaining a bite registration and includes a maxillary tray appliance and optionally a mandibular tray appliance. The maxillary tray appliance includes a first contacting portion that extends downwardly from a first base portion. The first contacting portion includes a first contacting surface, a first ridge line, and a first ridge line midpoint. The optional mandibular tray appliance includes a second contacting portion that includes a second contacting surface, a second ridge line, and a second ridge line midpoint. The first contacting portion and second contacting portion contact each other when a patient bites down with the maxillary tray appliance and the mandibular tray appliance situated in the patient's mouth.

15 Claims, 19 Drawing Sheets

(51) Int. Cl.
  *A61C 19/05* (2006.01)
  *A61C 13/00* (2006.01)
  *A61C 13/34* (2006.01)

(56) References Cited

U.S. PATENT DOCUMENTS

| | | | |
|---|---|---|---|
| 2,301,358 A | 11/1939 | Ballard | |
| 2,618,853 A | 11/1952 | Singer et al. | |
| 3,644,996 A | 2/1972 | Weinkle | |
| 3,813,777 A | 6/1974 | Van Handel et al. | |
| 4,227,877 A | 10/1980 | Tureaud et al. | |
| 4,235,594 A | 11/1980 | Schwartz | |
| 4,259,074 A | 3/1981 | Link | |
| 4,401,616 A | 8/1983 | Wagner | |
| 5,076,785 A | 12/1991 | Tsai | |
| 5,186,624 A | 2/1993 | Gottsleben | |
| 6,106,285 A | 8/2000 | Kwak | |
| 6,261,248 B1 | 7/2001 | Takaishi et al. | |
| 6,315,555 B1 | 11/2001 | Bortolotti | |
| 6,422,864 B1 | 7/2002 | Glatt | |
| 6,929,473 B2 | 8/2005 | Kwon et al. | |
| 7,174,895 B2* | 2/2007 | Thornton | A61F 5/566 128/848 |
| 8,070,489 B2* | 12/2011 | Massad | A61C 19/05 433/71 |
| 8,277,216 B2* | 10/2012 | Kim | A61C 9/0006 433/37 |
| 8,376,738 B2 | 2/2013 | Wagner | |
| 8,425,229 B2 | 4/2013 | Nilsson et al. | |
| 8,459,990 B2 | 6/2013 | Massad | |
| 8,801,431 B2 | 8/2014 | Thompson | |
| 8,899,983 B2 | 12/2014 | Kim | |
| 8,998,615 B2* | 4/2015 | Kim | A61C 9/0006 433/214 |
| 9,226,806 B2 | 1/2016 | Manai et al. | |
| 9,326,834 B2 | 5/2016 | Morales et al. | |
| 9,358,083 B2 | 6/2016 | Clausen et al. | |
| 9,370,318 B2 | 6/2016 | Linguraru et al. | |
| 9,402,698 B2 | 8/2016 | Thompson | |
| 9,433,483 B2 | 9/2016 | Suga et al. | |
| 9,498,310 B2 | 11/2016 | Suga et al. | |
| 9,675,432 B2 | 6/2017 | Lee et al. | |
| 2006/0172254 A1 | 8/2006 | Shindo et al. | |
| 2007/0231774 A1 | 10/2007 | Massad | |
| 2009/0246729 A1 | 10/2009 | Massad | |
| 2010/0020073 A1 | 1/2010 | Corazza et al. | |
| 2010/0297572 A1 | 11/2010 | Kim | |
| 2012/0015330 A1 | 1/2012 | Zhivago | |
| 2012/0077141 A1 | 3/2012 | Massad | |
| 2012/0258426 A1 | 10/2012 | Boe | |
| 2013/0209962 A1 | 8/2013 | Thompson et al. | |
| 2013/0218530 A1 | 8/2013 | Deichmann et al. | |
| 2014/0051037 A1 | 2/2014 | Fisker | |
| 2014/0255873 A1 | 9/2014 | Bullis et al. | |
| 2014/0277665 A1 | 9/2014 | Fisker | |
| 2014/0308624 A1 | 10/2014 | Lee et al. | |
| 2016/0008106 A1 | 1/2016 | Chiou et al. | |
| 2016/0095677 A1 | 4/2016 | Morales et al. | |
| 2016/0166362 A1 | 6/2016 | Nonboe et al. | |

OTHER PUBLICATIONS

ISA/US, International Search Report and Written Opinion on PCT/US18/22243, May 24, 2018, U.S. Patent and Trademark Office, Alexandria, Virginia, US.

* cited by examiner

ALIGNING APPARATUS USED IN FABRICATING DENTAL PROSTHESES

CROSS-REFERENCE TO RELATED APPLICATIONS

This application claims the benefit of U.S. Provisional Application No. 62/512,075, filed 29 May 2017, which is hereby incorporated herein in its entirety.

TECHNICAL FIELD

In the field of dentistry, an apparatus is disclosed that is useful in fabricating dental prostheses, and in dental diagnosis where it is advantageous to obtain an accurate spatial configuration of a maxillary jaw in comparison to a mandibular jaw, with particularly useful application to an individual that is edentulous in at least a maxillary jaw.

BACKGROUND ART

A typical individual, or patient, has both a mandible (lower jaw or jawbone) and a maxilla (upper jaw). The lower jawbone is the strongest and lowest bone in the human face and it holds the lower teeth in place. The mandible is the only movable bone in the human skull and it is positioned beneath the maxilla. The mandible rotates about a hinge axis. The mandible may also undergo translational movement, i.e. moving forward, left, right, upward, downward etc.

Traditionally, making, for example, dentures takes at least 5 appointments, and include various steps, such as obtaining impressions, fabricating wax rims, adjusting the wax rims, setting teeth, and fabricating dentures.

Other methods for making dentures include use of edentulous tray systems with bite determining assemblies. One such edentulous tray system includes a pin and striking plate assembly, such as described in U.S. Pat. No. 8,070,489 to Massad. Another edentulous tray system includes projecting parts located on lateral portions of maxillary and mandibular trays, such as described in U.S. Pat. No. 9,498,310 to Suga.

SUMMARY OF INVENTION

A tray appliance system usable for obtaining a bite registration for a patient includes a maxillary tray appliance and optionally a mandibular tray appliance. Optionally, the maxillary tray appliance includes at least one tooth form.

The maxillary tray appliance includes a first base portion that includes a first top surface opposed to a first bottom surface. The first base portion additionally includes a first middle portion being substantially U shaped in a top view.

The first base portion includes a first medial portion that is upwardly extending with slope of at least 10 degrees from a medial side of the first middle portion. The first base portion further includes a first transverse midline in a bottom view and a first base portion anterior end.

Optionally, the first base portion includes a first lateral portion that is upwardly extending with slope of at least 10 degrees from a lateral side of the first middle portion. Optionally, the maxillary tray appliance includes a first occlusal extending portion where at least a portion of the first occlusal extending portion is located in a premolar area to a molar area. Optionally, the first base portion defines at least one aperture.

The maxillary tray appliance further includes a first contacting portion that extends downwardly from the first base portion. This first contacting portion includes a first contacting surface, which is elongate in a bottom view in that it has an anterior-posterior length that is at least twice as long as a transverse width in a bottom view. The first contacting portion makes contact with a surface originating from a mandibular jaw of the patient when the patient bites down.

The first contacting surface includes a first ridge line having an anterior-posterior length of no less than 10 millimeters and optionally between 15 and 60 millimeters. Optionally, the first contacting surface is downwardly converging in transverse cross sectional view but may also be straight or downwardly diverging. The first ridge line includes a first ridge line midpoint. Optionally, the first ridge line is straight in longitudinal cross sectional view but also may be arcuate, multi-sided, or wave-like in longitudinal cross sectional view. When the first ridge line is wave-like, it includes between 10 and 200 ridges. Optionally, the tray appliance is configured so that the vertical distance between the first ridge line and a patient's maxillary gum is between 3 millimeters to 20 millimeters. Optionally, the first contacting surface includes a first contacting surface width that is no more than 15 millimeters.

The first ridge line midpoint is located anterior to the first transverse midline in a bottom view. The first ridge line midpoint is also located posterior to the first base portion anterior end. Optionally, the first base portion has a first base portion length between 45 millimeters and 90 millimeters.

The optional mandibular tray appliance includes a second base portion that is U shaped in a bottom view. The second base portion includes a second top surface opposed to a second bottom surface.

The second base portion includes a second longitudinal midline wherein the second ridge line crosses the second longitudinal midline at 80 degrees to 100 degrees in a top view. The second base portion may further include a second transverse midline and a second base portion anterior end.

The optional mandibular tray appliance further includes a second contacting portion that extends upwardly from the second base portion. The second contacting portion includes a second contacting surface with a transverse length that is at least twice as long as an anterior-posterior width in a top view. The second contacting surface includes a second ridge line. The second ridge line may include a second ridge line midpoint. The second ridge line midpoint is preferably located anterior to the second transverse midline and posterior to the second base portion anterior end.

The first contacting portion and second contacting portion contact each other when a patient bites down with the maxillary tray appliance and the mandibular tray appliance situated in the patient's mouth.

Technical Problem

It is well known in the art that for the fabrication of dental prostheses and dental diagnosis, the mandible should be situated in a centric relation position. That is, the mandible should not be shifted anteriorly, downwardly, or laterally.

It is difficult for clinicians to record the relationship of the patient's maxillary jaw and mandibular jaw in the centric relation position. Patients often posture the mandible anteriorly when the clinician tries to obtain a bite registration. In order to posture the patient's mandible in the centric relation position, the clinician may instruct the patient to relax the facial muscles, and allow the clinician to push the mandible back. This technique, however, is often unsuccessful in posturing the patient into the centric relation position.

Rolling the tongue back is one method to position the patient in a centric relation position. Rolling the tongue back works to position the patient in a centric relation position because the muscles of the neck, such as genioglossus muscle, digastric muscle, mylohyoid muscle, stylohyoid muscle, superior belly of the omohyoid muscle, and the like apply a rearward force to the mandible.

However, finding a centric relation position by rolling back the tongue is ineffective when the patient does not roll the tongue sufficiently rearward. For example, the patient may position the tongue in a state of being partially rolled back, rather than being fully rolled back. When the tongue is partially rolled back, such as rolling the tongue upward within an anterior portion of the oral cavity, no rearward force is applied to the mandible. The clinician may go back and forth repeating instructions to the patient to position his/her tongue further back, with the patient not understanding the instructions, or not being able to roll the tongue sufficiently rearward.

Some prior art methods, such as described in U.S. Pat. No. 2,481,203 to Davies and in U.S. Pat. No. 8,070,489 to Massad, incorporate a pin and striking plate tracing system, which is positioned in a central area of the oral cavity. One problem is that this area is normally taken up by the tongue. The pin and striking plate tracing system often pushes the tongue down. This in turn causes several problems. First, because the tongue is a strong muscle, it will exert an upward force on the pin and striking plate tracing system, causing it to become unstable. Second, the tongue will be restricted in its motion, and will not be able to roll back into the fully rolled back position.

Some prior art methods for obtaining a bite in an edentulous individual incorporate edentulous tray systems (such as U.S. Pat. No. 9,498,310 to Suga) which include projecting parts located on lateral portions of the trays. It is often a problem when utilizing these trays that one side contacts before the other. When a patient bites down and makes contact on one side, there is a tendency to shift the mandible laterally, to make contact in the projecting parts on an opposing side. The patient, therefore, brings the mandible into a position where the mandible is postured anteriorly and laterally. This anterior and lateral position of the mandible is not ideal for making dental prostheses or dental diagnosis. Additionally, when the patient bites down, the edentulous trays will easily dislodge on a side opposite the side of contact.

Some prior art edentulous tray systems (such as described in U.S. Pat. No. 6,196,840 to Zentz) cannot accommodate different jaw sizes, such as patients having retrognathic or prognathic jaw configurations, and/or patients having more bone resorption on one side of the maxilla and/or mandible than the other side.

Additionally, some tray systems have many different components, and may be difficult to use and/or are expensive to produce.

Yet additionally, some tray systems (such as described in U.S. Pat. No. 9,498,310 to Suga) cannot be used for patients having anatomical discrepancies from the norm, such as more bone loss on one side of the mouth than the other, joint problems, and the like.

Solution to Problem

The solution is a tray system or aligning apparatus which accurately captures: a transverse jaw relationship; a vertical jaw relationship; and optimal displacement of musculature in the mouth.

Advantageous Effects of Invention

The disclosed tray system may be useful for fabrication of a dental prosthetic, such as a denture, an overdenture, an implant bridge, and the like.

The disclosed tray system may be used for both taking an impression and capturing a jaw relationship.

The disclosed tray system may deliver accuracy in capturing jaw relationships while requiring minimum adjustment by a clinician.

The disclosed tray system may provide space for the tongue.

The disclosed tray system may prevent off center biting by the patient.

The disclosed tray system may allow obtaining an accurate jaw registration when the maxillary tray appliance and/or mandibular tray appliance is (are) slightly misaligned.

The disclosed tray system may have few components.

The disclosed tray system may allow for rotational and/or translational freedom to accommodate different jaw sizes and/or jaw relationships.

The disclosed tray system may provide a jaw registration in an appropriate occlusal vertical dimension.

The disclosed tray system may be light in weight and does not dislodge easily in the mouth.

The disclosed tray system may be economical.

The disclosed tray system may allow the patient to visualize what a denture to be fabricated may look like in the mouth.

Some aspects of the disclosed tray system may provide varying occlusal vertical dimension depending on jaw discrepancy.

Some aspects of the disclosed tray system may prevent movement during setting of jaw registration material.

Some aspects of the disclosed tray system may allow for visualization to check for complete seating in the mouth and/or on a dental cast.

Some aspects of the disclosed tray system may be especially well suited for patients having anatomical deviations from the norm.

Some aspects of the disclosed tray system may be useful for medical and dental diagnosis, such as diagnosing optimal dental implant locations, diagnosing need for bone removal or augmentation in preparation for dental implant placement, and/or constructing a surgical template to aid in dental implant placement.

BRIEF DESCRIPTION OF DRAWINGS

The drawings illustrate preferred embodiments of the aligning apparatus, also referred to as a tray appliance system, according to the disclosure.

DESCRIPTION OF EMBODIMENTS

In the following description, reference is made to the accompanying drawings, which form a part hereof and which illustrate several embodiments of the present invention. The drawings and the preferred embodiments of the invention are presented with the understanding that the present invention is susceptible of embodiments in many different forms and, therefore, other embodiments may be utilized and structural, and operational changes may be made, without departing from the scope of the present invention.

Definitions

Upward and downward: Throughout this description, the terms upward and/or upwardly describe a generally upward direction from the perspective of a person standing on the ground. The upward direction may indicate a direction that is upward and medial, upward and lateral, upward and anterior, upward and posterior, upwardly curving in any direction, and the like, as appropriate. Similarly, the downward direction may indicate a direction that is downward and medial, downward and lateral, downward and anterior, downward and posterior, downward curving in any direction, and the like, as appropriate.

Horizontal plane: Throughout this description, the term horizontal plane indicates a plane parallel to a patient's Camper's Plane during use.

Edentulous: Throughout this description, the term edentulous describes a state of being substantially without teeth. That is, a state of being either: completely without teeth; or completely without teeth, but having at least one dental implant.

Occlusal vertical dimension: Throughout this description, the term occlusal vertical dimension describes a relationship of an individual's maxilla to the individual's mandible, as commonly defined in the field of dentistry.

Patient and/or individual: Throughout this description, the terms "patient" and "individual" describes a person who is seeking dental treatment and/or dental diagnosis.

Clinician: Throughout this description, the term clinician describes a user of the tray appliance system of the present invention. The clinician may be, for example, a dentist, a dental technician, a dental assistant, any dental professional, the patient's friend or relative, or the patient him/herself.

Figure 1:
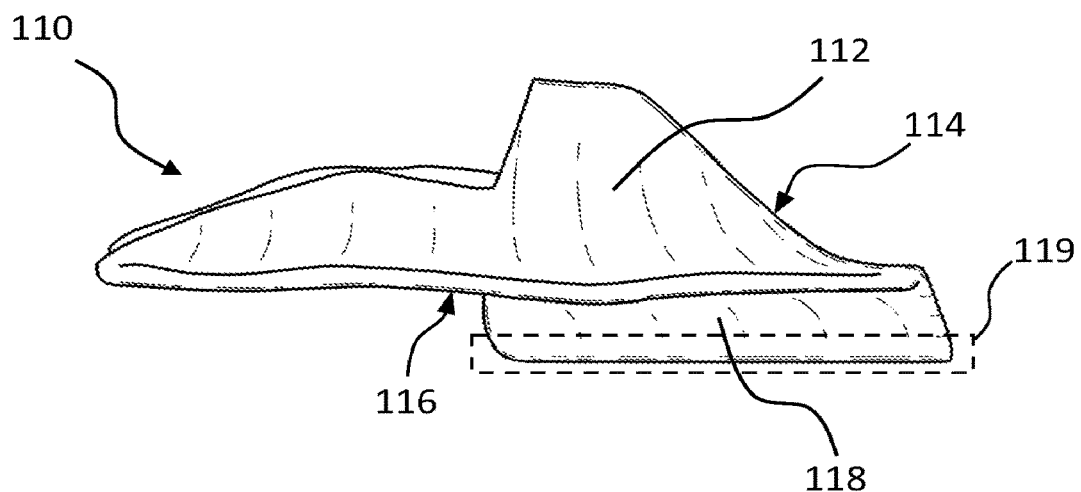
FIG. 1 is a side view of a tray appliance system including a maxillary tray appliance.

FIG. 1 illustrates an embodiment of a tray appliance system, which includes a maxillary tray appliance (110), shown in a side view. The maxillary tray appliance (110) includes a first base portion (112), which includes a first top surface (114) and a first bottom surface (116). The first top surface (114) is on the other side of, or opposed to, the first bottom surface (116), shown in the bottom view of the maxillary tray appliance (110) of FIG. 6. The first base portion (112) is preferably 0.5 millimeters to 5 millimeters in thickness. The first base portion (112) may be a portion of the maxillary tray appliance (110) that is substantially uniform in thickness. As will be described later, various different components may extend from the first base portion (112).

Figure 3:
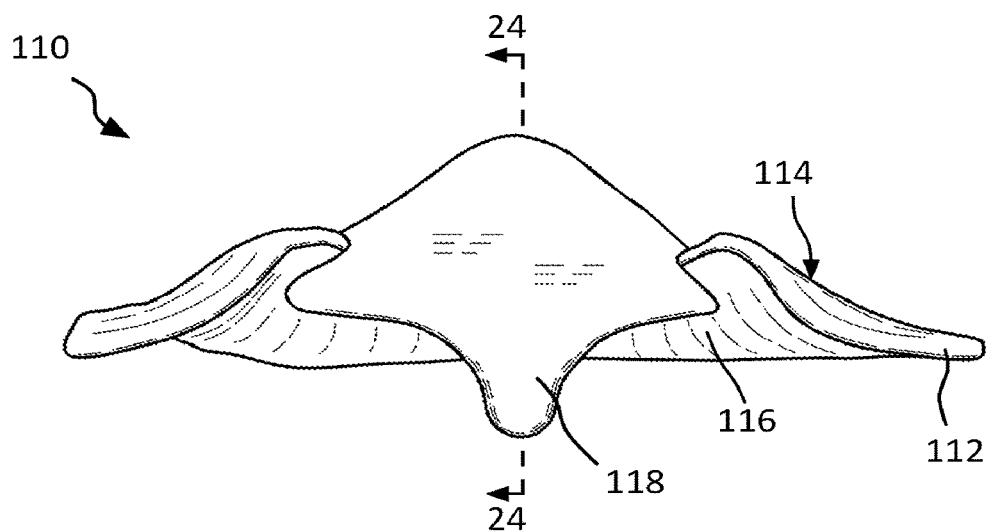
FIG. 3 is a rear view of the maxillary tray appliance of FIG. 1.

As best shown in FIG. 3, which is a rear view of the maxillary tray appliance (110), a first contacting portion (118) extends downwardly from the first base portion (112). In FIG. 24A, FIG. 24B, FIG. 24C, and FIG. 24D, the first dashed line (516) indicates a hypothetical location of the first bottom surface (116) that is integrated into the maxillary tray appliance (110). As previously described, the first base portion (112) preferably has a thickness of 0.5 millimeters to 5 millimeters.

The first contacting portion (118) serves to make contact with a surface originating from a mandibular jaw, which may be, for example: (1) a second contacting surface (149) of a second contacting portion (148) (which will be described later, see FIG. 12 and FIG. 25), or (2) a top surface of a mandibular tooth; or (3) a top surface of a mandibular gum.

As a rule, ordinal-number modifiers used herein do not indicate any rank or importance, but rather are a label to distinguish over other similarly-named parts discussed infra. Thus, the term "first" in the forgoing instance of "first base portion (112)" is simply a means for distinguishing the component's name.

Hereinafter, the maxillary tray appliance (110) may be referred to simply as "the tray".

Figure 4:
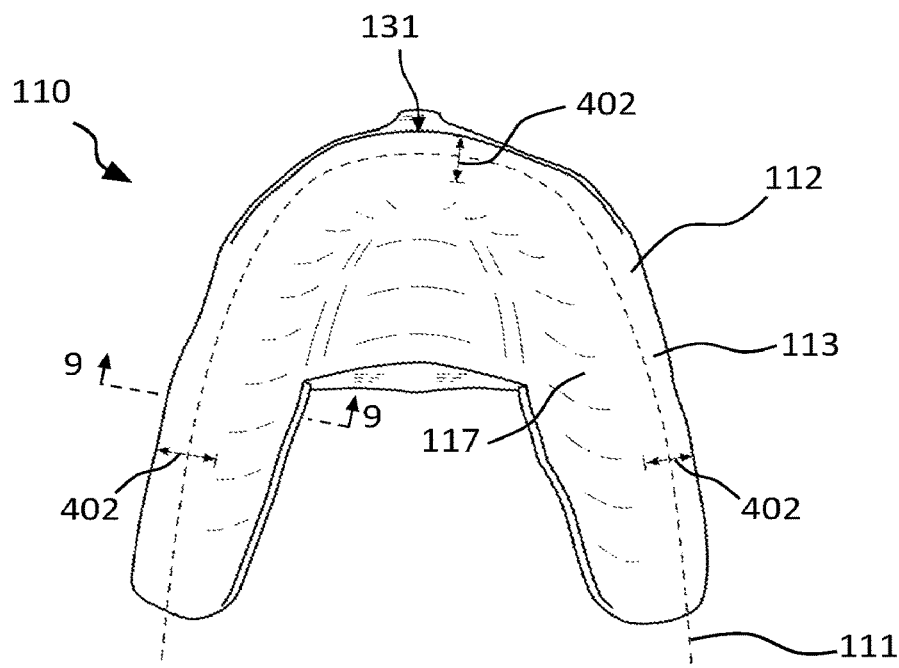
FIG. 4 is a top view of the maxillary tray appliance of FIG. 1.

Referring to FIG. 4, the first base portion (112) includes a first middle portion (113) which is substantially U shaped in a top view of the maxillary tray appliance (110). This is indicated by the dotted line indicating a first U shaped path (111) for the first middle portion (113). The first middle portion (113) may have first width (402), measured from a top view perpendicular to the first U shaped path (111) in different locations along the first U shaped path (111). As shown, first width (402) of the first middle portion (113) may be variable in different areas of the tray, which may be, for example, 1 mm to 40 mm. Throughout this disclosure, the units "mm" stand for millimeters.

Figure 5:
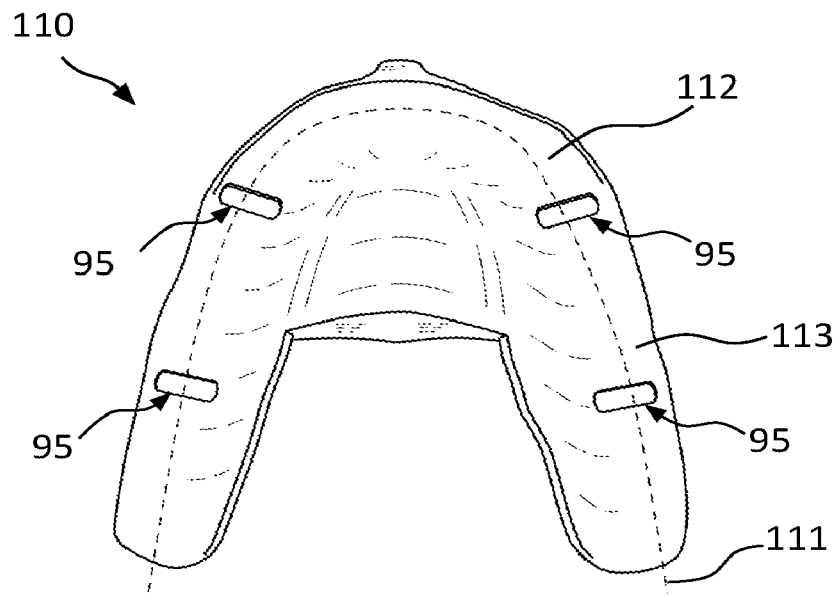
FIG. 5 shows an example of a maxillary tray appliance having at least one aperture according to the embodiment of FIG. 4.

Throughout this disclosure, the term "substantially U shaped" indicates a shape which is in the form of either a continuous U or a discontinuous U, having any width, length, and/or curvature. As shown in FIG. 5, the first base portion (112) may define at least one aperture, as indicated by a first aperture (95). The aperture(s) may be used for, for example, retaining impression material, that is, allowing impression material to pass through to provide increased retention between the impression material and the tray. The aperture(s) may be any shape, such as an elongated slot as shown, a circular shape, a rectangular shape, and the like. The aperture(s) may be located anywhere on the first base portion (112). Thus, in the embodiment shown in FIG. 5, the first middle portion (113) has a discontinuous U shape.

Figure 9:
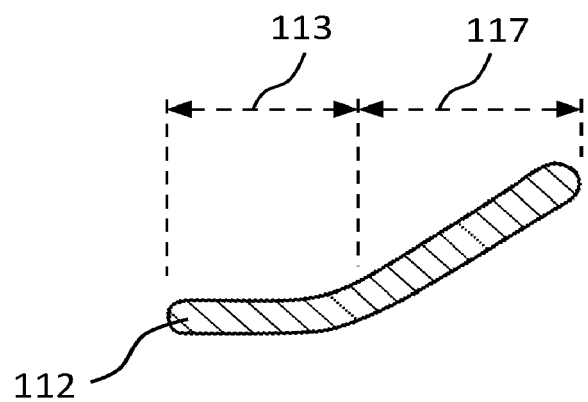
FIG. 9 is a cross-sectional view of the maxillary tray appliance of FIG. 1 taken through section 9-9 of FIG. 4.

As shown in FIG. 4, the first base portion (112) additionally includes a first medial portion (117), being upwardly extending with slope of at least 10 degrees from a medial side of the first middle portion (113) (see also FIG. 9).

The first base portion (112) serves to either: make contact with the edentulous maxilla of an individual; or support impression material to be applied to the edentulous maxilla of an individual.

When the first base portion (112) is used to support impression material, the first base portion (112) may be contoured such that the first base portion (112) provides a suitable amount of space depending on the type of material. As well known in the art, different impression materials have different suitable thicknesses. For example, alginate impression material may require more space than, for example, light body polyvinyl siloxane impression material. Therefore, the contour of the first base portion (112) may be a function of intended use.

FIG. 9 is an illustration representing a sectional view of the maxillary tray appliance (110) through section 9-9 of FIG. 4. More specifically, section 9-9 is a section transverse to the first U shaped path (111) (as shown in FIG. 4). Returning to FIG. 9, the first middle portion (113) has an upward slope of no more than 10 degrees from the horizontal plane. Thus, the first medial portion (117) extends generally upwardly from the medial side of the first middle portion (113) at an upward slope of more than 10 degrees at the junction of the first medial portion (117) and the first middle portion (113). As best shown in FIG. 3, the first base portion (112) may be contoured to accept a palate of an edentulous individual, or provide a suitable amount of space for impression material to be applied thereto.

Returning to FIG. 4, the size of the first U shaped path (111) may be a function of patient anatomy (such as size of the patient's edentulous maxilla) and/or intended use (that is, whether the tray is intended to make contact with an edentulous maxilla or used to carry impression material).

Preferably, the first medial portion (117) and the first middle portion (113) are integral portions of the first base portion (112). However, it is contemplated that the first medial portion (117) and the first middle portion (113) may be separate pieces. That is, first base portion (112) may be formed in two or more pieces, removably joined to each other. This configuration may be advantageous for use in, for example, patients who are prone to gagging. The first base portion (112) being formed in separate pieces may be more comfortable for the patient during a try-in procedure, and would thus enable obtaining a more accurate jaw registration. The first base portion (112) being formed in one piece may be more resistant to fracture, and less difficult to manufacture.

Although in the embodiment shown in FIG. 9, the first middle portion (113) and first medial portion (117) join each other in the form of a continuous arc (when viewed in cross section), in some embodiments, the first middle portion (113) and the first medial portion (117) may join each other in other configurations, such as an L-shaped junction.

Additionally, the first medial portion (117) may be present in only some portions of first base portion (112). For example, first medial portion (117) may be present in only an anterior half of the first base portion (112). This configuration, for example, may be especially advantageous for use in a patient who has a maxillary torus and/or for a patient who is prone to gagging. The first medial portion (117) may be present in only a posterior half of the first base portion (112). This configuration may be used for patients who have a maxillary torus that is located in an anterior half of the maxillary palate. The aforementioned configurations advantageously contribute to the accuracy of jaw registration for patients having the aforementioned exemplary conditions.

Figure 30:
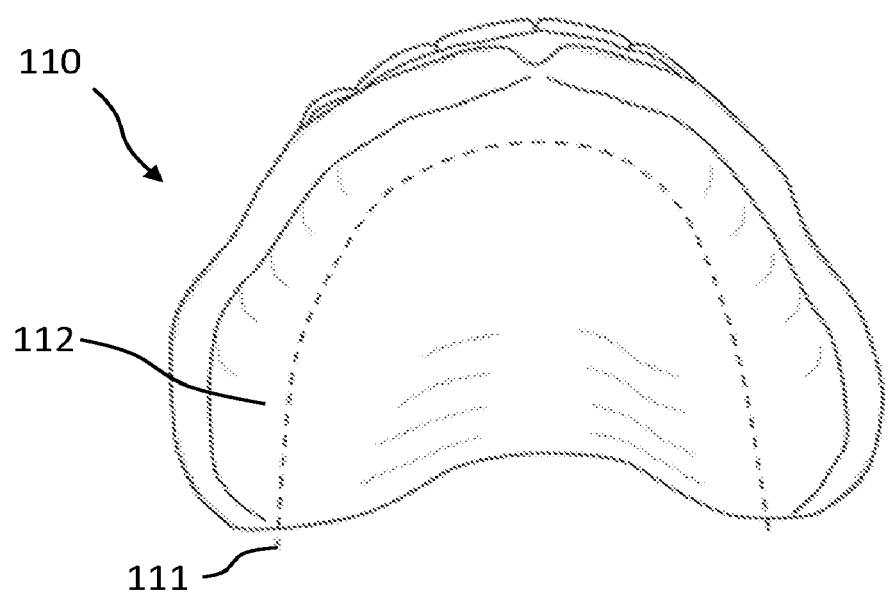
FIG. 30 is a top view of the maxillary tray appliance of FIG. 25.

As shown in FIG. 4, in some embodiments, the first base portion (112) may have a U shaped form when viewed from the top. In some embodiments, such as shown in FIG. 30, the first base portion (112) may have a generally semi-elliptical form when viewed from the top. The generally semi-elliptical form as shown serves to cover a large percentage (such as more than 80 percent) of surface area of the patient's edentulous maxilla, which serves to provide increased retention between the maxillary tray appliance (110) and the patient's edentulous maxilla, and/or allow impression material to be applied to a large percentage of surface area of the patient's edentulous maxilla.

The U shaped form and generally semi-elliptical form of the first base portion (112) may be preferable in different situations. For example, when a maxillary denture is to be fabricated for a patient who does not have a palatal torus, and who is not prone to gagging, the generally semi-elliptical form may be preferred. For example, when a prosthesis is to be made for a patient who has a prominent gag reflex, the U shaped form may be preferred.

Figure 10:
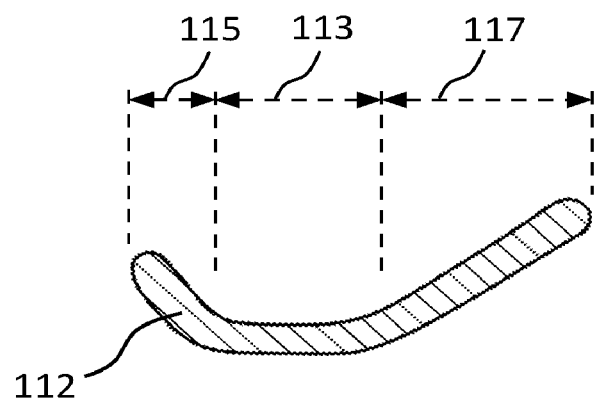
FIG. 10 shows an example of a maxillary tray appliance having a first lateral portion according to the embodiment of FIG. 9.
Figure 27:
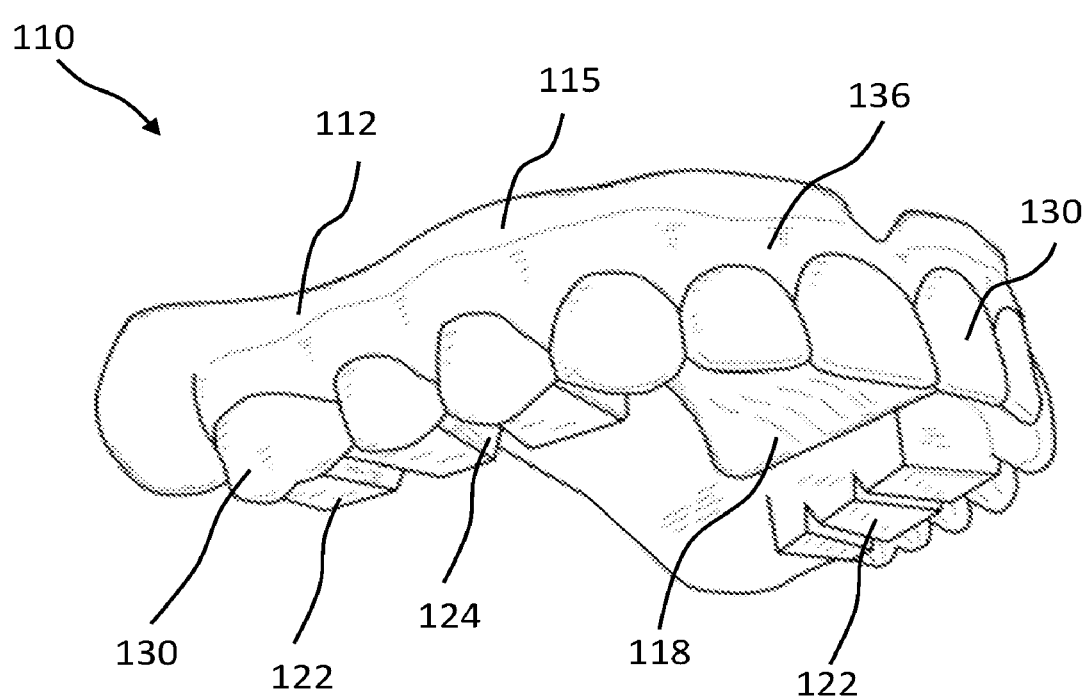
FIG. 27 is a bottom perspective view of the maxillary tray appliance of FIG. 25.

Referring to FIG. 10, in some embodiments, the first base portion (112) may include a first lateral portion (115), which extends generally upwardly from a lateral side of the first middle portion (113). As described previously, the first middle portion (113) has an upward slope of no more than 10 degrees. Thus, the first lateral portion (115) extends generally upwardly from the lateral side of the first middle portion (113) at an upward slope of more than 10 degrees (from the horizontal plane). FIG. 27 illustrates one embodiment of the maxillary tray appliance (110) which includes the first lateral portion (115).

The first lateral portion (115) may serve, for example, to allow an impression to be taken of the patient's entire edentulous maxillary gum. Additionally, the first lateral portion (115) may serve to provide increased retention between the maxillary tray appliance (110) and the patient's maxillary gum. Yet additionally, the first lateral portion (115) may serve to simulate a maxillary denture flange. It is well known in the art that a denture flange may push the patient's upper lip out in a lateral direction. Therefore, providing the first lateral portion (115) will allow the patient to visualize what a denture to be fabricated may look like in the mouth.

Figure 7:
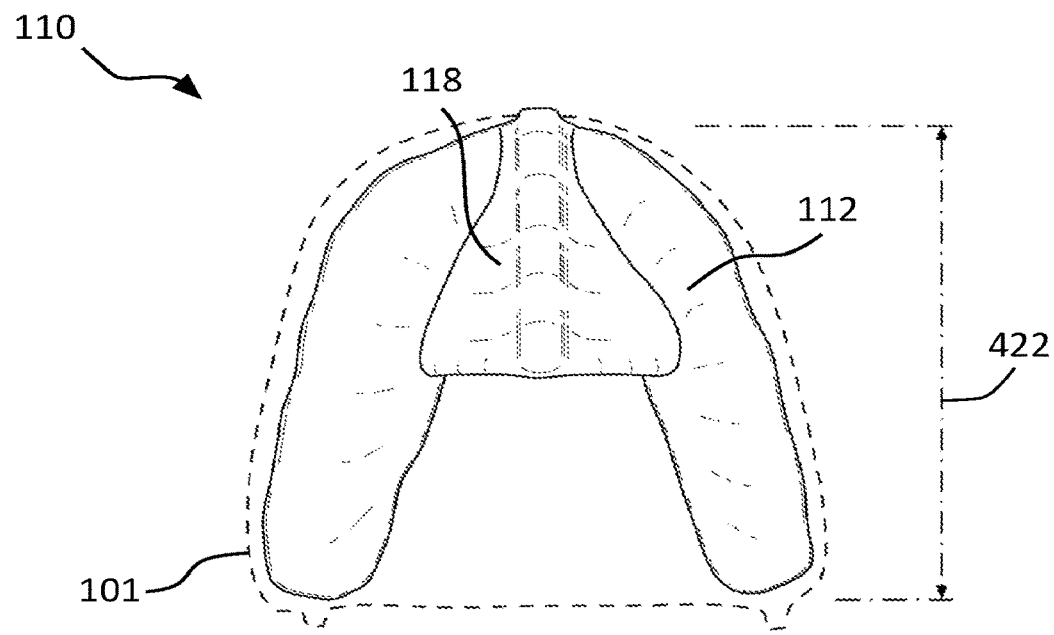
FIG. 7 is a bottom view of the maxillary tray appliance of FIG. 1 showing relative size of a typical human edentulous maxilla.
Figure 8:
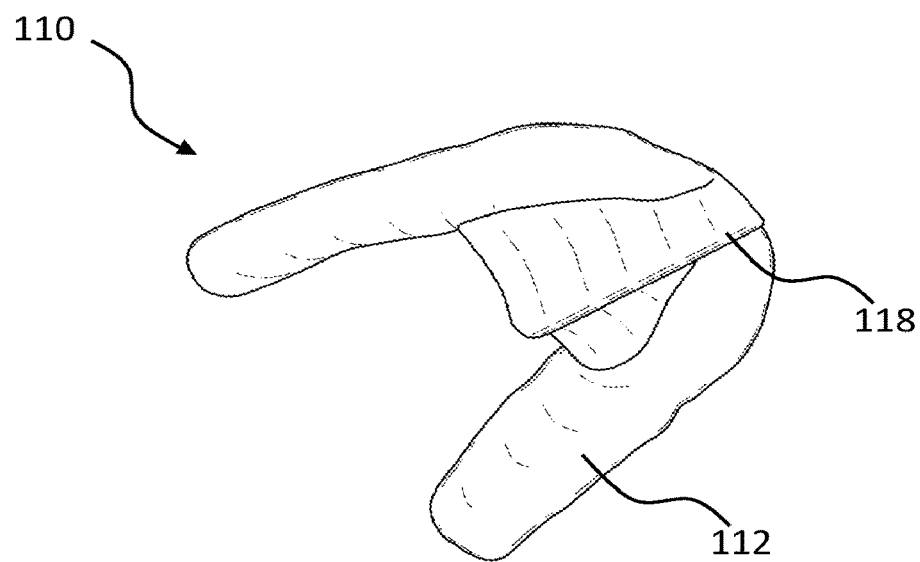
FIG. 8 is a bottom perspective view of the maxillary tray appliance of FIG. 1.

As shown in FIG. 7, the first base portion (112) has a first base portion length (422), measured anterior-posteriorly, that is 80% to 120% of an anterior-posterior length of a typical human edentulous maxilla (101) (indicated by the dashed enclosure in FIG. 7) when viewed from the bottom. In almost all instances, this translates to the first base portion length (422) that is between 45 millimeters and 90 millimeters.

As commonly defined in dentistry, the anterior-posterior length of a typical human edentulous maxilla is defined as a measurement from an anterior end of the edentulous maxilla to an imaginary line connecting the patient's two hamular notches, measured parallel to Camper's Plane.

It has been determined that if the first base portion length (422) is more than ninety (90) millimeters, the maxillary tray appliance (110) will be too large, and the patient may gag, and/or the patient's upper lip may prevent maxillary tray appliance (110) from being placed against the individual's edentulous maxilla comfortably. It has been determined that if the first base portion length (422) is less than forty-five (45) millimeters, the maxillary tray appliance (110) may be too small, and/or may be easily dislodged, and/or may not cover enough of the patient's edentulous maxilla to obtain an accurate impression.

In some embodiments, the maxillary tray appliance (110) may be custom made to fit an individual's edentulous maxilla, such as by 3D printing, milling, using a light cured material, using a chemically cured material, or any combination(s) thereof. In some embodiments, at least a portion of the maxillary tray appliance (110) may be made in a thermoplastic material, and may be adapted to fit the individual's edentulous maxilla.

In some embodiments, a plurality of sizes may be made available, such as a small, medium, and large size.

Figure 11:
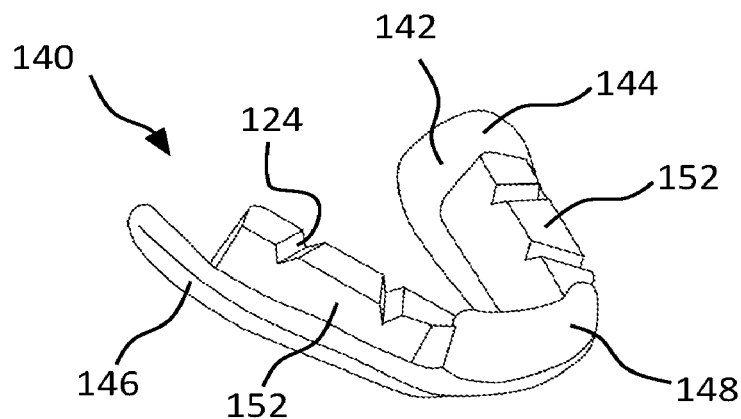
FIG. 11 is a top perspective view of a mandibular tray appliance.
Figure 19A:
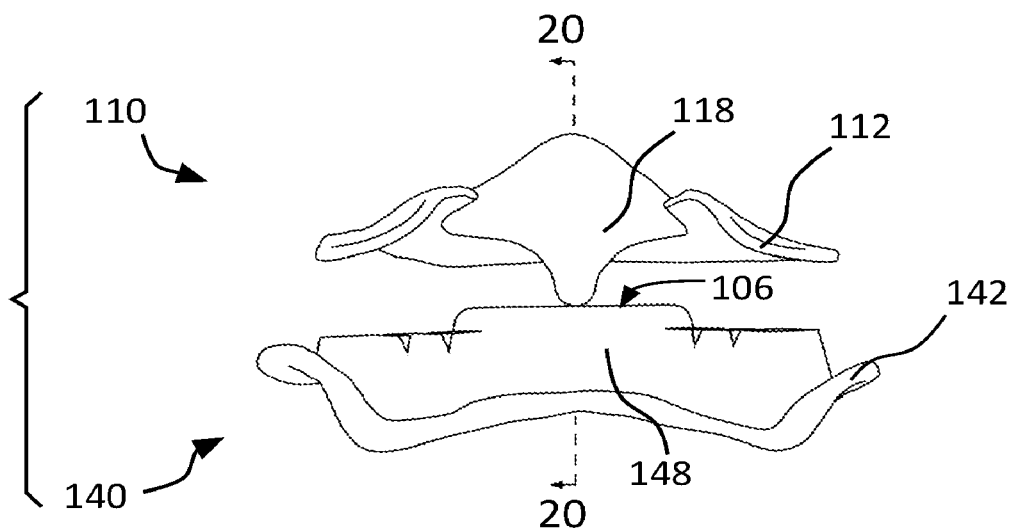
FIG. 19A is a rear view of a tray appliance system showing the maxillary tray appliance of FIG. 1 and the mandibular tray appliance of FIG. 11.
Figure 25:
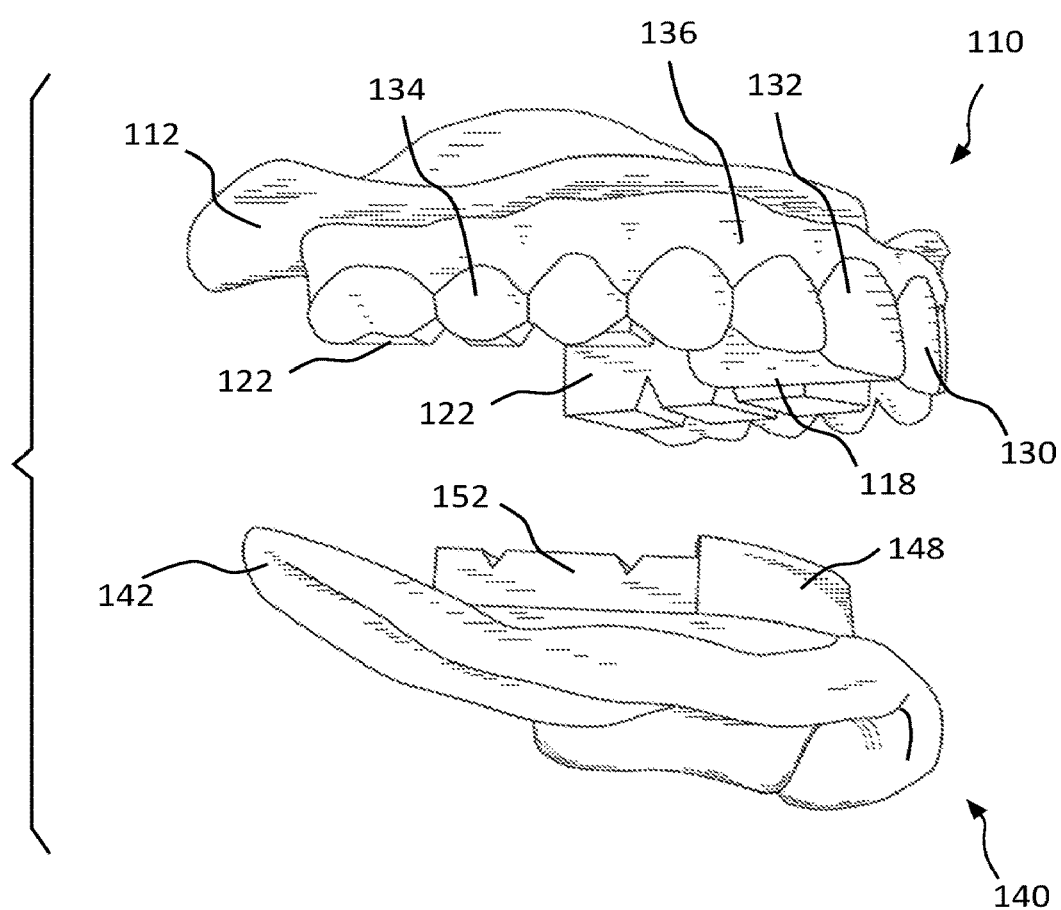
FIG. 25 is an exploded side perspective view of an embodiment of a tray appliance system including a maxillary tray appliance and a mandibular tray appliance.
Figure 26:
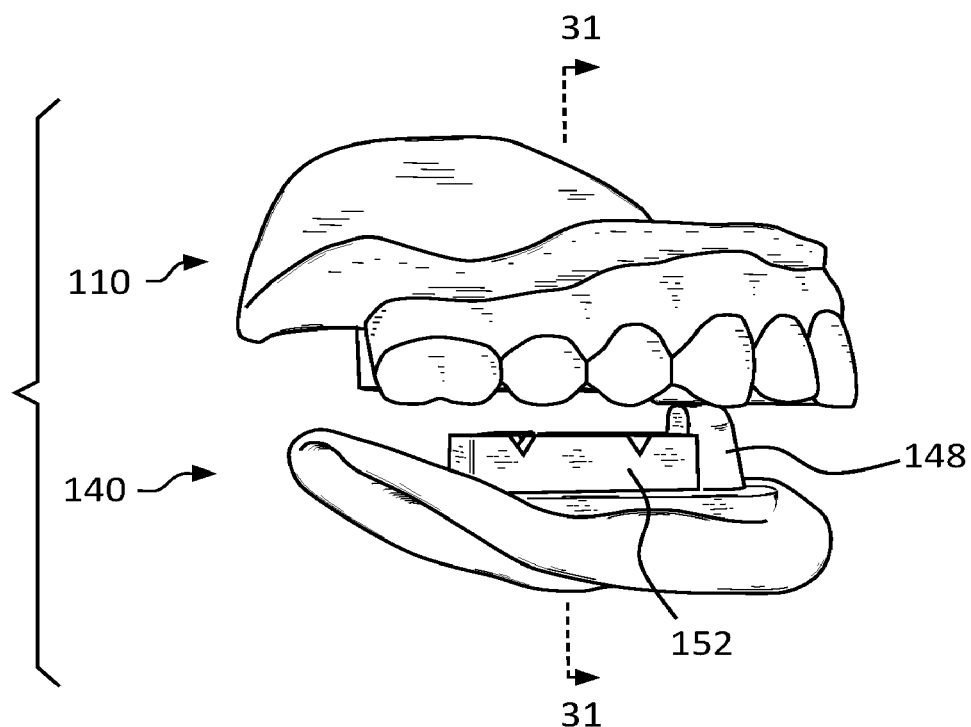
FIG. 26 is a side view of the tray appliance system of FIG. 25.

Referring now to FIG. 11, a mandibular tray appliance (140) may be used in conjunction with the maxillary tray appliance (110) (see FIG. 19A). Specifically, the mandibular tray appliance (140) may be used when the patient is completely edentulous. According to some embodiments, FIG. 19A and FIG. 25 illustrate different embodiments of the tray appliance system, which may include the maxillary tray appliance (110) and the mandibular tray appliance (140). As described previously, the tray appliance system may also include only the maxillary tray appliance (110) (that is, without the mandibular tray appliance (140), see FIG. 1).

As shown in FIG. 11, the mandibular tray appliance (140) includes a second base portion (142). The second base portion (142) is preferably 0.5 millimeters to 5 millimeters in thickness. The second base portion (142) includes a second bottom surface (146), shown in FIG. 13, and a second top surface (144), shown in FIG. 14 and FIG. 15. A second contacting portion (148) extends upwardly from the second base portion (142). As shown in FIG. 19A, the second contacting portion (148) serves to make contact with the first contacting portion (118) of the maxillary tray appliance (110). The second base portion (142) may be a portion of the mandibular tray appliance (140) that is substantially uniform in thickness. As will be described later, various different components may extend from the second base portion (142).

Figure 13:
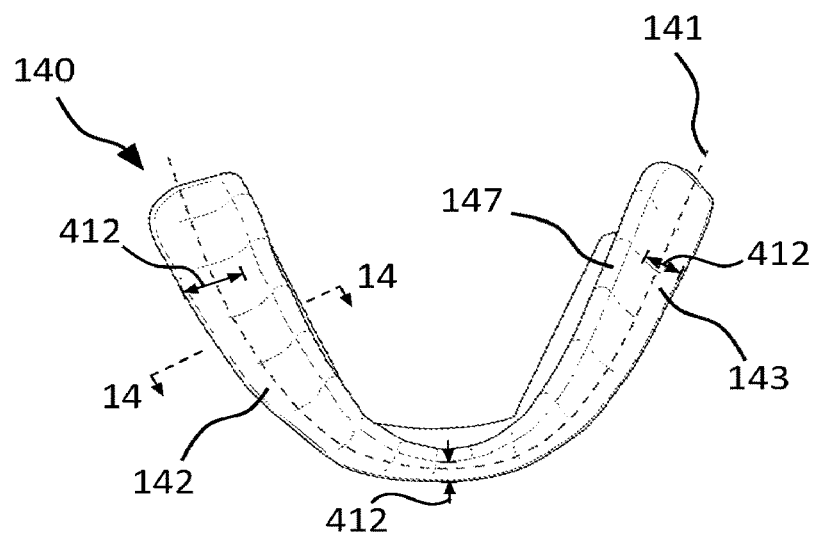
FIG. 13 is a bottom view of the mandibular tray appliance of FIG. 11.

As shown in FIG. 13, the second base portion (142) is preferably U shaped in a bottom view. As in integral unit, the second base portion (142) may include a second middle portion (143) being substantially U shaped in a bottom view. The second middle portion (143) follows a second U shaped path (141) for the second middle portion (143). The second middle portion (143) may have a second width (412), measured from a bottom view transverse to second U shaped path in different locations. As shown, the second width (412) of the second middle portion (143) may be variable in different areas of the mandibular tray appliance (140), which may be, for example, 1 mm to 40 mm.

Figure 14:
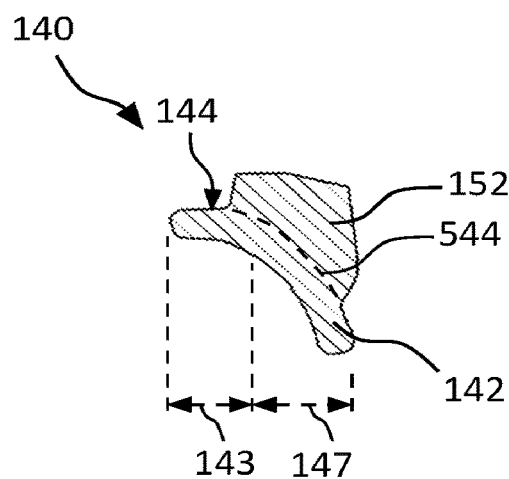
FIG. 14 is a cross-sectional view of the mandibular tray appliance of FIG. 11 taken through section 14-14 of FIG. 13.

FIG. 14 is an illustration representing a sectional view of the mandibular tray appliance (140) through section 14-14 in FIG. 13. More specifically, section 14-14 is a section transverse to the second U shaped path (141) (as shown in FIG. 13). A second dashed line (544) in FIG. 14 indicates a hypothetical location for the second top surface (144) that is integrated into the mandibular tray appliance (140).

As shown in FIG. 14, the second middle portion (143) has a downward slope of no more than 10 degrees. A second medial portion (147), which may be an integral part of the second base portion (142), and which may extend generally downwardly from a medial side of the second middle portion (143) at a downward slope of more than 10 degrees at the junction of the second middle portion (143) and the second medial portion (147).

As shown in FIG. 13, the size of the second U shaped path (141) may be a function of patient anatomy (such as size of the patient's edentulous mandible) and/or intended use (that is, whether the mandibular tray appliance (140) is intended to make contact with an edentulous mandible or used to carry impression material).

Preferably, the second medial portion (147) and the second middle portion (143) are integral portions of the second base portion (142). However, it is contemplated that second medial portion (147) and the second middle portion (143) may be separate pieces.

Figure 15:
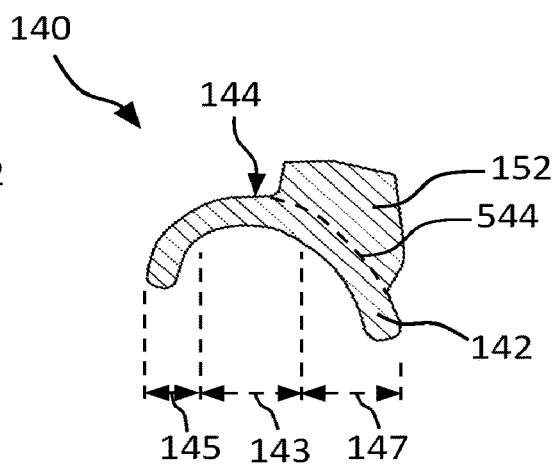
FIG. 15 shows an example of a mandibular tray appliance having a second lateral portion according to the embodiment of FIG. 14.

Referring to FIG. 15, in some embodiments, the second base portion (142) may additionally include a second lateral portion (145), which may be an integral part of the second base portion (142), and which extends generally downwardly from a lateral side of the second middle portion (143). The second lateral portion (145) may serve to simulate a mandibular denture flange. It is well known in the art that a denture flange may push the patient's lower lip out in a lateral direction. Therefore, providing the second lateral portion (145) will allow the patient to visualize what a denture to be fabricated may look like in the mouth. Additionally, the second lateral portion (145) may allow an impression to be taken of the patient's entire edentulous mandibular gum.

Figure 34:
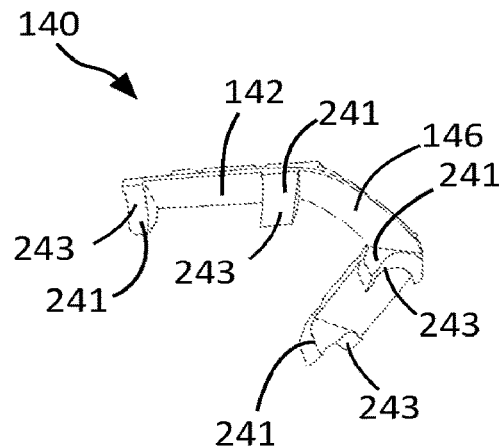
FIG. 34 is a bottom perspective view of the mandibular tray appliance of FIG. 32.

Referring to FIG. 34, in some embodiments, the second medial portion (147) and/or the second lateral portion (145) may not be present. In some embodiments, the second base portion (142) may be substantially flat (that is, having a slope of no more than 10 degrees in cross sectional view).

Figure 19B:
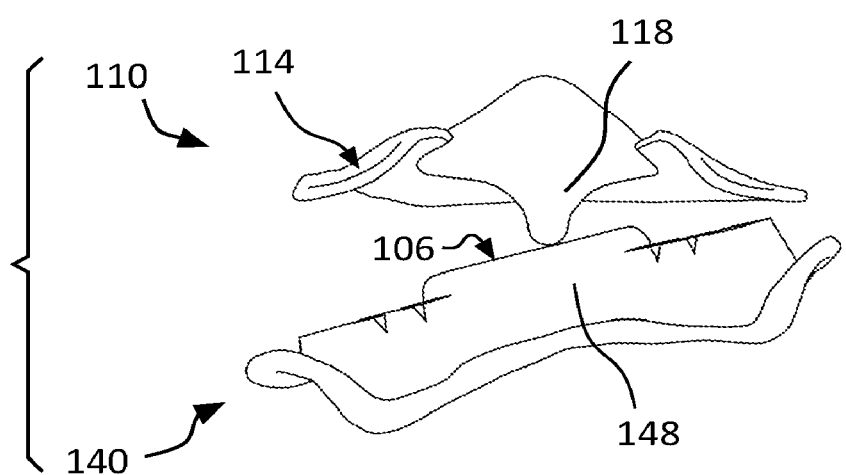
FIG. 19B is a rear view of the tray appliance system of FIG. 19A showing use in a patient with more bone resorption on one side of the mandible than the other side.

FIG. 19B is a rear perspective view of the tray appliance system of FIG. 19A showing use in a patient who has, for example, more bone loss on one side of the mandible than the other side. Since, during the process of jaw registration, it is not known what the precise relationship between the maxillary and mandibular jaws are, it is advantageous for the tray appliance system to accommodate rotational and translational differences from the norm. For example, the configuration shown in FIG. 19B may be useful in a patient who has had more bone loss on one side of the mandible (such as a left side) than another side of the mandible (such as a right side). Since patients have teeth extracted for varying reasons, such as tooth decay, tooth infection, periodontal disease, trauma, and the like, it is common to have more bone loss on one side (e.g. of the mandible) than another side.

Additionally, when an impression material is to be applied to the tray appliance system, such as an impression material applied to the first top surface (114) of the maxillary tray appliance (110), the clinician may push with more force on one side of the maxillary tray appliance (110) than the other side when the impression material is setting. This may cause the maxillary tray appliance (110) to be rotationally misaligned to the maxilla, that is, one side of the maxillary tray appliance (110) may be lower than the other side of the maxillary tray appliance (110). This misalignment may cause a lateral aspect of the maxillary tray appliance (110) and a lateral aspect of the mandibular tray appliance (140) to contact each other, instead of the first contacting portion (118) and the second contacting portion (148) making contact. If the lateral aspect of the maxillary tray appliance (110) and the lateral aspect of the mandibular tray appliance (140) were to make contact, the maxillary tray appliance (110) and/or the mandibular tray appliance (140) may be dislodged, that is, separate from contact with the patient's gum. This would result in an inaccurate jaw registration, and may lead to a dental prosthesis that does not have an accurate occlusion.

Figures 20A, 20B:
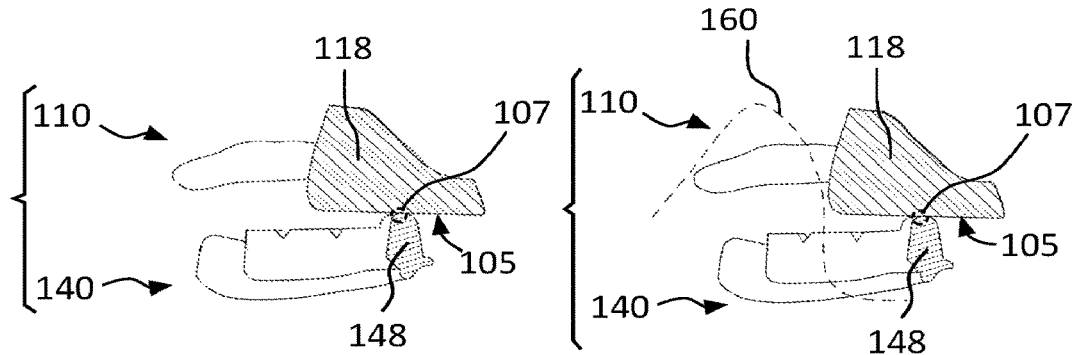
FIG. 20A is a cross-sectional view of the tray appliance system of FIG. 19A taken through section 18-18 of FIG. 19A.
FIG. 20B is the cross-sectional view of the tray appliance system of FIG. 20A showing the position of the patient's tongue in a rolled back position.
Figures 20C, 20D:
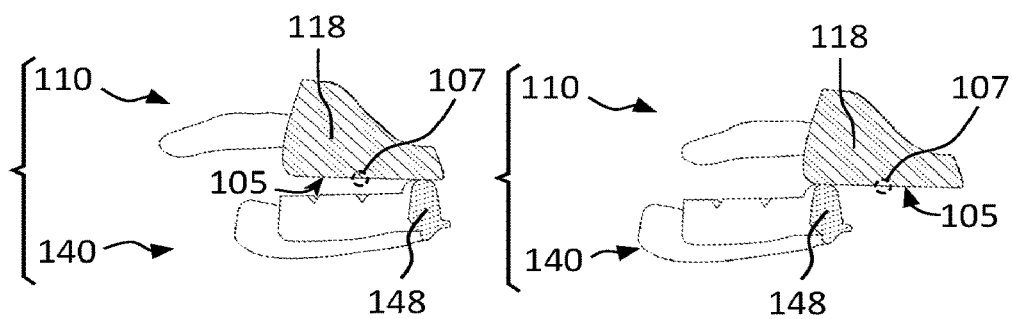
FIG. 20C is the cross-sectional view of the tray appliance system of FIG. 20A showing use in a patient with a prognathic jaw configuration.
FIG. 20D is the cross-sectional view of the tray appliance system of FIG. 20A showing use in a patient with a retrognathic jaw configuration.

Thus, one advantage of most embodiments is the advantage of having rotational freedom. That is, being able to be used in a variety of rotational differences from the norm (such as shown in FIG. 19B). A second advantage of most embodiments is the advantage of having translational freedom. That is, being able to be used in a variety of translational differences from the norm (such as shown in FIG. 20C and FIG. 20D).

Figure 2:
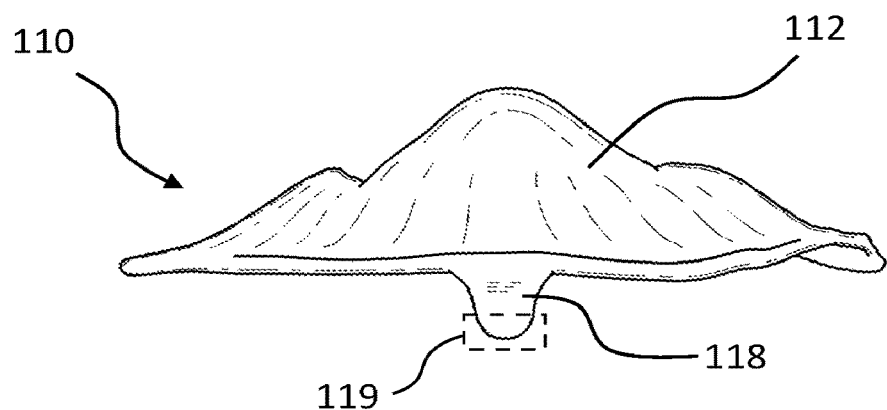
FIG. 2 is a front view of the maxillary tray appliance of FIG. 1.
Figure 6:
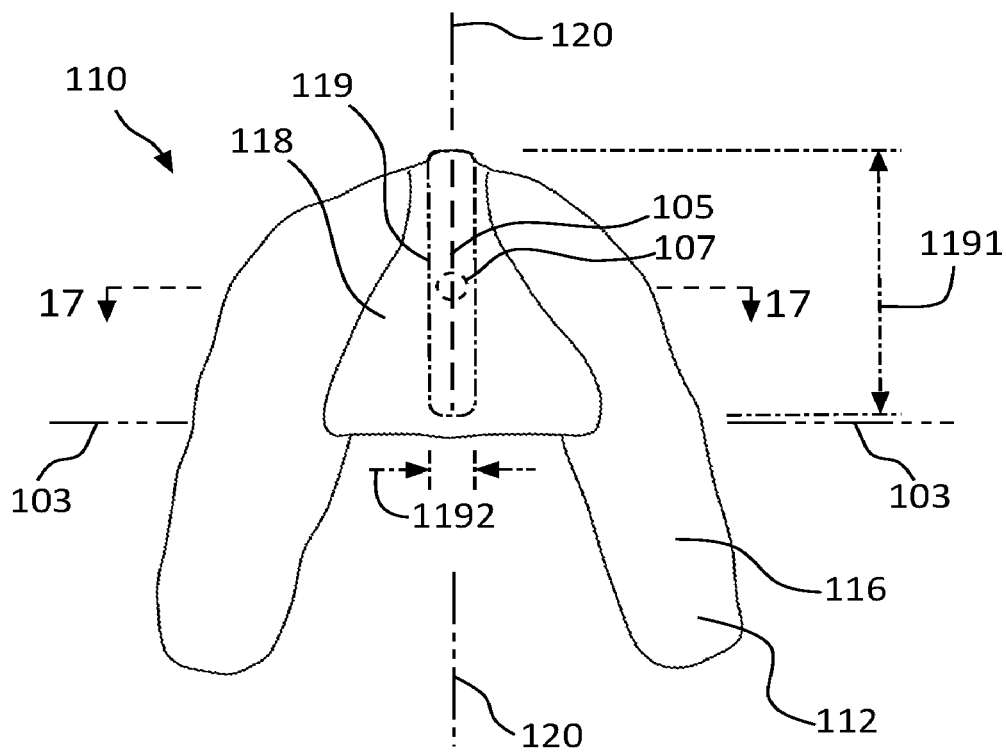
FIG. 6 is a bottom view of the maxillary tray appliance of FIG. 1.

Returning to FIG. 1, FIG. 2, and FIG. 6, the first contacting portion (118) includes a first contacting surface (119). FIG. 1, FIG. 2, and FIG. 6 show the first contacting surface (119) outlined by dashed line enclosures, respectively.

Figure 28:
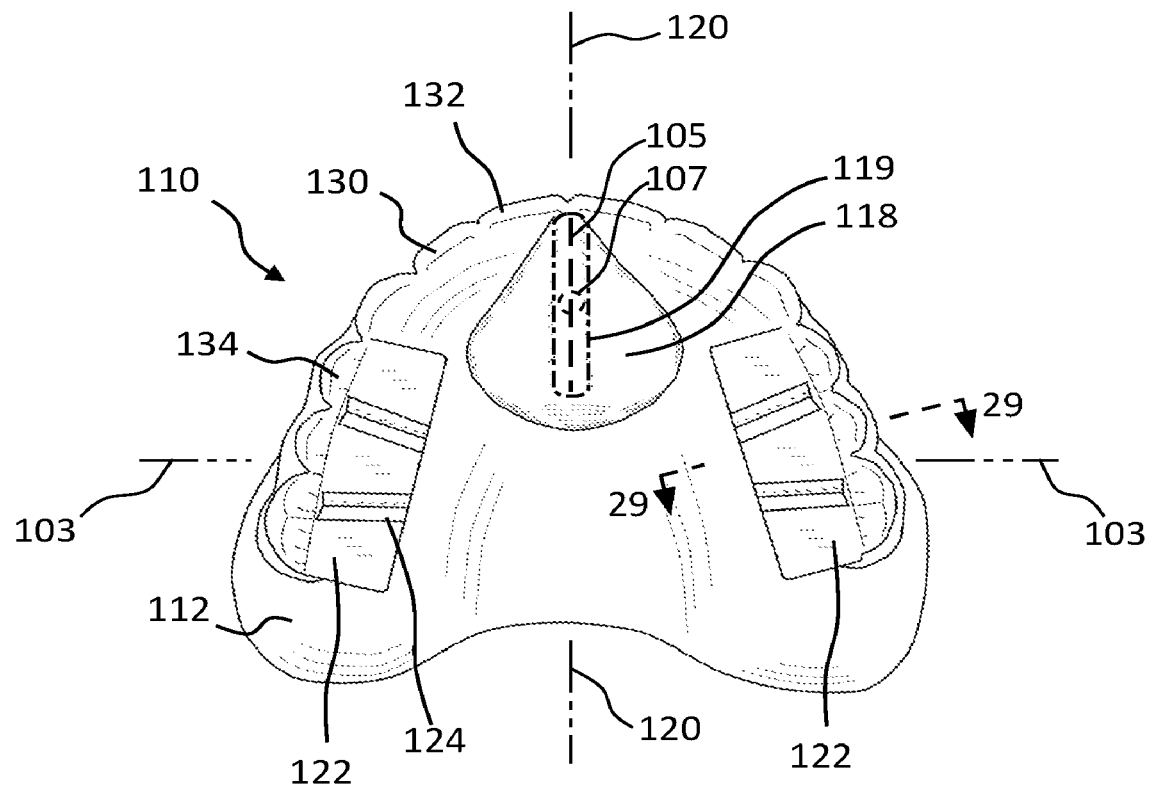
FIG. 28 is a bottom view of the maxillary tray appliance of FIG. 25.

As shown in FIG. 6 and FIG. 28, the first contacting surface (119) includes a first ridge line (105).

Figure 17:
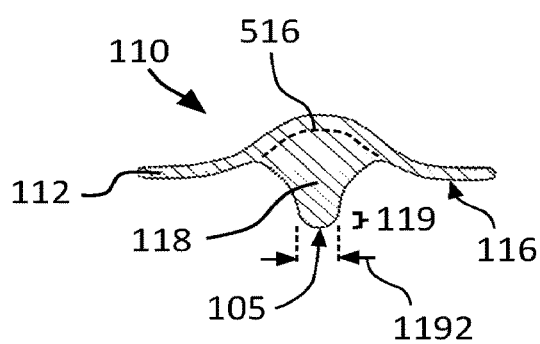
FIG. 17 is a cross-sectional view of the maxillary tray appliance of FIG. 1 taken through section 17-17 of FIG. 6.

FIG. 17 shows a section of the maxillary tray appliance (110) through section 17-17 of FIG. 6. Specifically, section 17-17 is a section transverse to the first ridge line (105). A first dashed line (516) in FIG. 17 indicates a hypothetical location for the first bottom surface (116) that is integrated into the maxillary tray appliance (110). The first contacting surface (119) is defined as a surface covering a bottom 2 (two) millimeters of the first contacting portion (118) when viewed in transverse cross section. As shown in FIG. 17 and FIG. 6, the first ridge line (105) may be defined as a line connecting bottom-most points of the first contacting surface (119) in successive transverse cross sections. As shown in FIG. 6, the first contacting surface (119) is preferably elongate in form. That is, the first contacting surface (119) is longer in an anterior-posterior direction than it is wide in a transverse direction. Preferably, the first contacting surface (119) is configured with an anterior-posterior length, also referred to as a first contacting surface length (1191) in FIG. 6, that is at least twice as long as a transverse width, also referred to as a first contacting surface width (1192) in FIG. 6, in a bottom view.

Since the purpose of the first contacting portion (118) is to contact the surface originating from the mandibular jaw, the elongate form of the first contacting surface (119) advantageously may serve to accommodate a variety of jaw configurations, such as orthognathic, prognathic, or retrognathic jaw configurations. Additionally and/or alternatively, the elongate form of the first contacting surface (119) may serve to direct vector forces during contact to be substantially centered (that is, not too far off to the left side or right side), thus preventing tipping of the tray and/or off-center biting by the patient.

Returning to FIG. 6, as described previously, the first contacting surface (119) includes the first contacting surface width (1192). As shown in FIG. 17, the first contacting surface width (1192) is defined as a greatest width of the first contacting surface (119) measured in a transverse direction in cross sectional view. The first contacting surface width (1192) is preferably no more than 15 millimeters, and more preferably no more than 10 millimeters.

It had been determined that if the first contacting surface width (1192) is more than 15 millimeters, it would be too wide, and may lead to dislodgement of the tray from the patient's maxillary jaw and/or off-center biting by the patient. The first contacting surface width (1192) being no more than 10 millimeters allows the point of contact to be even closer to the patient's sagittal midline, and advantageously prevents dislodgement of the tray.

As shown in FIG. 23A, FIG. 23B, FIG. 23C, FIG. 23D, FIG. 23F, FIG. 23G, FIG. 23H, and FIG. 23I, it is preferable but not essential that the first contacting surface (119) is downwardly converging in cross sectional view.

The downwardly converging form of the first contacting surface (119) advantageously serves to provide resistance to fracture or bending when the patient bites down while allowing for a point of contact (that is, between the maxillary tray appliance (110) and the surface originating from the mandibular jaw) to be close to the patient's mid sagittal plane, which in turn prevents off center biting by the patient and/or prevents the maxillary tray appliance (110) from dislodgment.

Figure 23A:
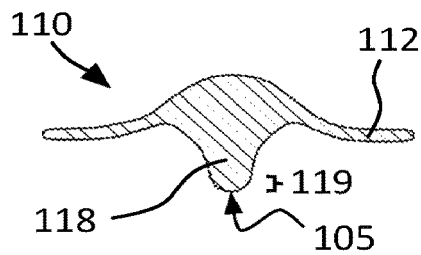
FIG. 23A is a cross-sectional view of the maxillary tray appliance of FIG. 1 taken through section 17-17 of FIG. 6.
Figure 23B:
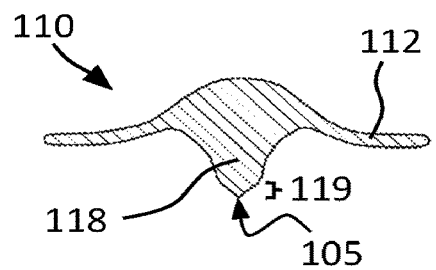
FIG. 23B illustrates an example of a first contacting surface that converges to a point.

Referring to FIG. 23A, more preferably, the first contacting surface (119) in transverse cross section may be substantially rounded. This substantially rounded form may include a radius of curvature that is, for example, between 0.5 millimeters to 25 millimeters, and more preferably, between 0.5 millimeters and 5 millimeters. It will be understood that the substantially rounded form of the first contacting surface (119) in cross section is not limited to a portion of a circle, but may be, for example, any rounded surface, such as, for example, a portion of an ellipse, a parabolic shape, and the like. This configuration may provide a contacting surface that is substantially parallel to the horizontal plane during contact with the surface originating from the mandibular jaw, and may further prevent off center biting by the patient and/or slipping of the tray.

Figure 23C:
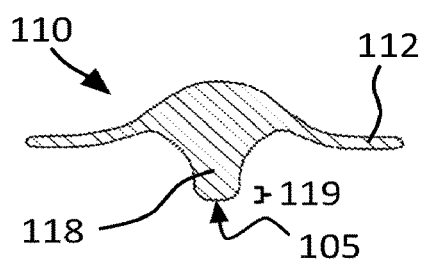
FIG. 23C illustrates an example of a first contacting surface that converges to a line in transverse cross section.
Figure 23D:
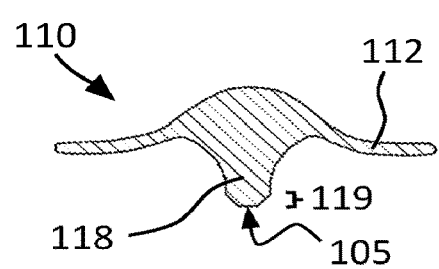
FIG. 23D illustrates another example of a first contacting surface that converges to a line in transverse cross section.
Figure 23E:
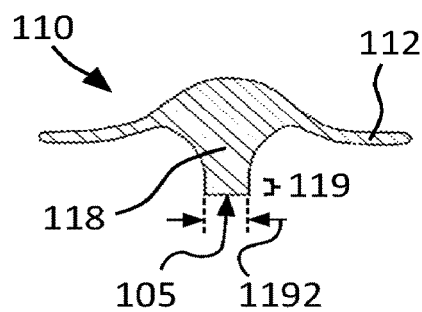
FIG. 23E illustrates another example of a first contacting surface that is straight in its downward form.
Figure 23F:
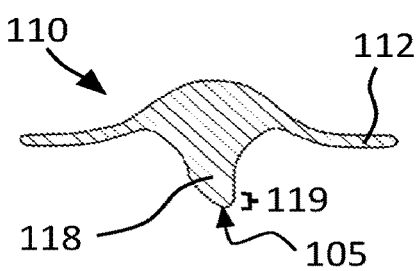
FIG. 23F illustrates an example of a first contacting surface that is skewed to the right side in transverse cross section.
Figure 23G:
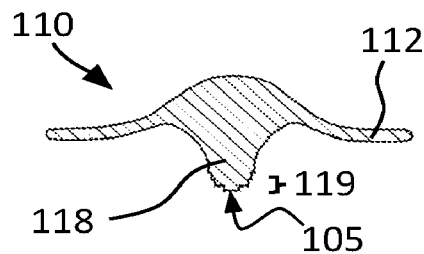
FIG. 23G illustrates another example of a first contacting surface that converges to a line in transverse cross section.

As shown in FIG. 23F, the first contacting surface may be skewed to one side, such as a right side or a left side in transverse cross section. This skewed form may be particularly advantageous for use in patients with a known mandibular jaw discrepancy, such as a discrepancy to a right side or a left side.

In some embodiments, the first contacting surface may include a bottom surface that is parallel to the horizontal plane. Thus, as shown in FIG. 23C, FIG. 23D, FIG. 23E, and FIG. 23G, the first contacting surface (119) may downwardly converge to a line in transverse cross section. In these embodiments, the first ridge line (105) may be defined as a line (when viewed from the bottom, see FIG. 6) connecting transverse midpoints of bottom-most lines of the first contacting surface (119) in successive transverse cross sections.

Embodiments shown in FIG. 23C, FIG. 23D, and FIG. 23E may be especially advantageous for use in, for example, a patient who is missing at least one mandibular anterior tooth, such as a mandibular central incisor. In this situation, the flat bottom surface allows a remaining mandibular anterior tooth to make contact with the first contacting surface (119). These embodiments may also be easier to manufacture by hand, such as using a light cured tray material (such as TRIAD tray material manufactured by DENTSPLY of York, Pa.).

Referring to FIG. 23E, in some embodiments, the first contacting surface (119) may also be downwardly diverging or straight. In these embodiments (that is, embodiments having downwardly diverging or straight first contacting surface (119)), the first contacting surface width (1192) is preferably no more than 10 millimeters, and more preferably no more than 7 millimeters. This dimension advantageously serves to prevent contact that is too far off center from the patient's mid-sagittal plane.

Figure 23H:
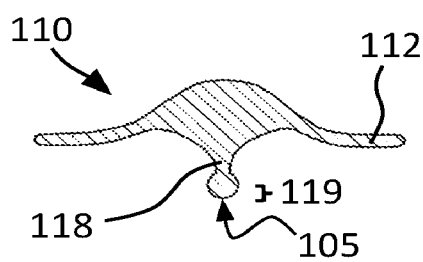
FIG. 23H illustrates an example of a first contacting portion that has a downwardly diverging form.
Figure 23I:
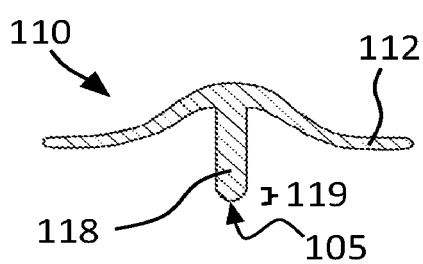
FIG. 23I illustrates an example of a first contacting portion that is straight in its downward form.

Referring to FIG. 23A, FIG. 23H, and FIG. 23I, the first contacting portion (118) is not particularly limited in cross sectional view. As shown in FIG. 23A, the first contacting portion (118) is preferably downwardly converging, serving to provide resistance to fracture and/or allow for rotational freedom. As shown in FIG. 23H, the first contacting portion (118) may also take a downwardly diverging form. As shown in FIG. 23I, the first contacting portion (118) may also take a straight form.

Figure 24A:
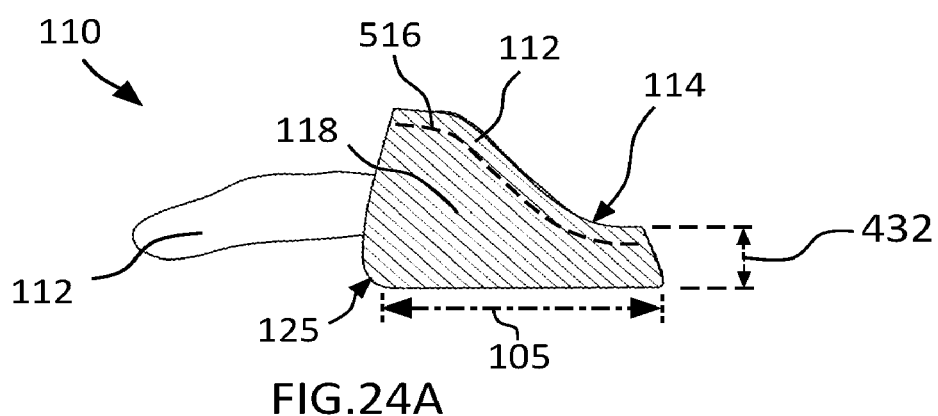
FIG. 24A is a cross-sectional view of the maxillary tray appliance of FIG. 1 taken through section 24-24 of FIG. 3, illustrating the first contacting portion having a rounded corner or bevel so as to provide a surface that does not harm the patient's tongue.
Figure 24B:
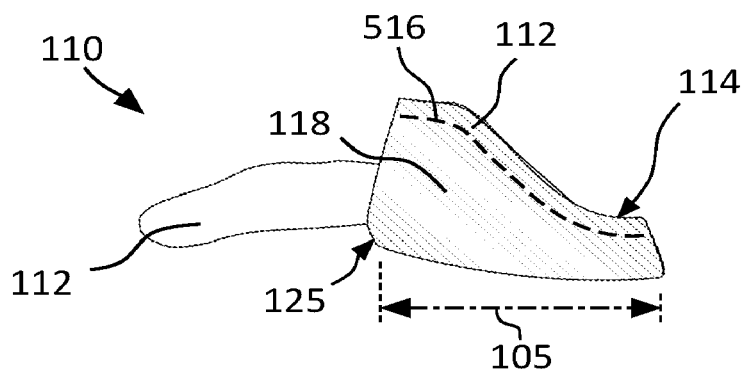
FIG. 24B is a cross-sectional view of the maxillary tray appliance of FIG. 1 taken through section 24-24 of FIG. 3, illustrating an upward inclination (from the horizontal plane) of no more than 30 (thirty) degrees of the first ridge line.
Figure 24C:
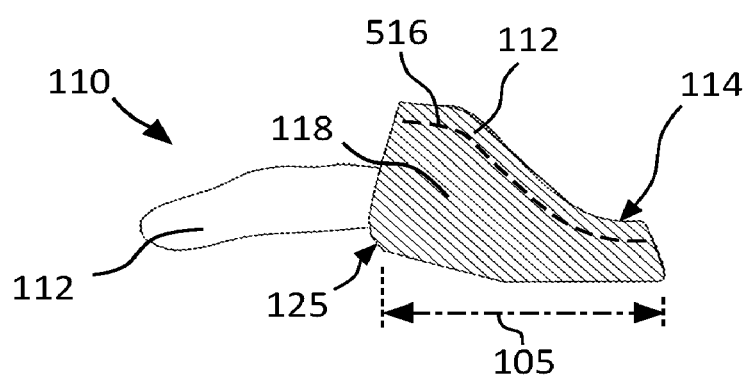
FIG. 24C is a cross-sectional view of the maxillary tray appliance of FIG. 1 taken through section 24-24 of FIG. 3, providing a second example of an upward inclination (from the horizontal plane) of no more than 30 (thirty) degrees of the first ridge line.

As shown in FIG. 24A and FIG. 24C, the first contacting portion (118) may include a first corner (125), which may be in the form of a rounded corner as shown in FIG. 24A or flat or multi-planar bevel shown in FIG. 24C, serving to provide a surface that does not hurt the patient's tongue. If the patient's tongue is hurt during use, the resulting jaw registration will not be accurate because of patient flinching.

The first corner (125) is not part of the first ridge line (105). The first ridge line (105) has an upward inclination (from the horizontal plane) of no more than 30 (thirty) degrees, serving to provide a suitable occlusal vertical dimension according to location of contact (between the first contacting surface (119) and the surface originating from the mandibular jaw).

The first ridge line (105) is preferably sufficiently long (anterior-posteriorly) to allow for the maxillary tray appliance (110) to be able to be used for a variety of different jaw sizes. This is illustrated in FIG. 20A, FIG. 20C, and FIG. 20D. FIG. 20A illustrates the embodiment shown in FIG. 19A in use in a patient with an orthognathic jaw relationship. FIG. 20C illustrates the embodiment shown in FIG. 19A in use in a patient with a prognathic jaw relationship. FIG. 20D illustrates the embodiment shown in FIG. 19A in use in a patient with a retrognathic jaw relationship. Returning to FIG. 6, a first ridge line length (anterior-posteriorly) of the first ridge line (105) is at least 10 millimeters, and more preferably at least 15 millimeters. It has been determined that the first ridge line length (anterior-posteriorly) of the first ridge line (105) being less than 10 millimeters will be too short, and will not be able to accommodate differences in jaw size relative to the norm (see FIG. 20C and FIG. 20D).

As shown in FIG. 6, the first base portion (112) includes a first longitudinal midline (120) and a first transverse midline (103). As shown in FIG. 4, the first base portion (112) includes a first base portion anterior end (131).

As shown in FIG. 6, the first ridge line (105) includes a first ridge line midpoint (107), which is defined as an anterior-posterior midpoint of the first ridge line (105). In FIG. 6, FIG. 20A, FIG. 20B, FIG. 20C, and FIG. 20D, the first ridge line midpoint (107) is outlined by dashed line enclosures, respectively.

As shown in FIG. 6, in a transverse direction, the first ridge line midpoint (107) is preferably within 15 (fifteen) millimeters of the first longitudinal midline (120) when viewed from the bottom. It has been determined that when the first ridge line midpoint (107) is within 15 (fifteen) millimeters, and more preferably within 5 millimeters in a transverse direction of the first longitudinal midline (120) of the maxillary tray appliance (110), the maxillary tray appliance (110) will: be less prone to dislodging from the patient's maxillary jaw; and/or be less prone to off-center biting by the patient; and/or provide more room for the clinician's fingers to press on the mandibular tray appliance (140).

As shown in FIG. 6, the first ridge line (105) is preferably substantially parallel (that is, within 10 degrees) with the first longitudinal midline (120). It had been determined that if the first ridge line (105) has an angle of more than 10 degrees from the first longitudinal midline (120), there will be increased chance of slipping and/or off-center biting by the patient, which, in turn, will lead to an inaccurate jaw registration.

Figure 12:
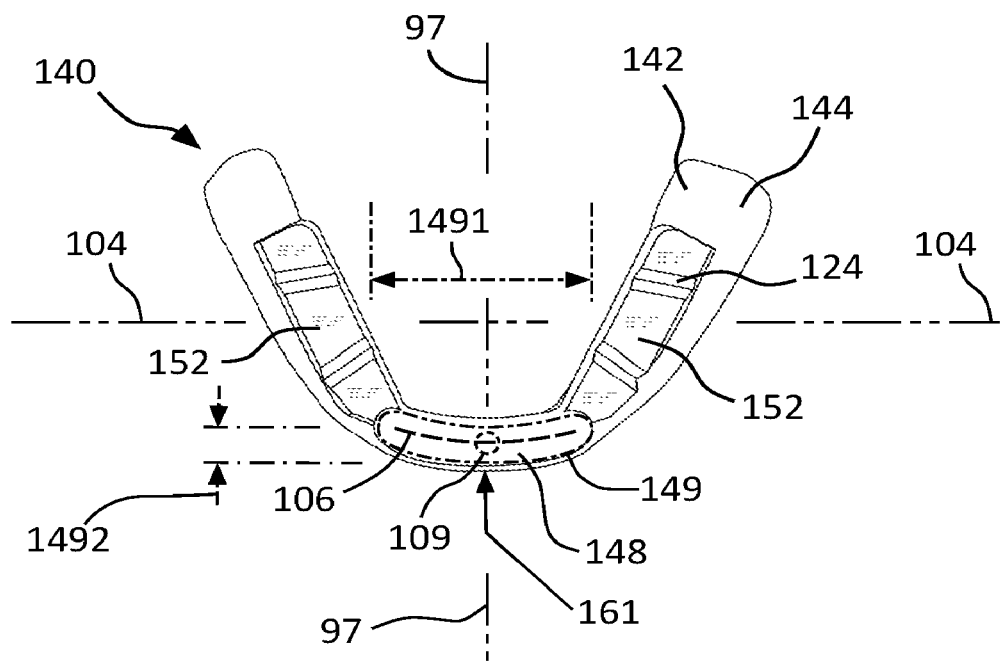
FIG. 12 is a top view of the mandibular tray appliance of FIG. 11.

As shown in FIG. 12, the second base portion (144) includes a second longitudinal midline (97) and a second transverse midline (104). The second base portion (142) additionally includes a second base portion anterior end (161).

The second contacting portion (148) includes a second contacting surface (149), which is elongate in a top view. In FIG. 12, the second contacting surface (149) is outlined by a dashed line enclosure. The second contacting surface (149) is preferably configured with a transverse length, also referred to as a second contacting surface length (1491) that is at least twice as long as an anterior-posterior width, also referred to as a second contacting surface width (1492), in a top view. The second contacting surface width (1492) of the second contacting surface (149) is measured anterior-posteriorly at the second longitudinal midline (97) in top view.

It was determined that when the second contacting surface length (1491) is at least twice as long as the second contacting surface width (1492), the second contacting surface (149) will allow for sufficient accommodation of differences in patient's maxillary and mandibular jaws to the bone in a lateral (left to right) direction, while providing sufficient room (anterior-posteriorly) for the tongue and lower lip.

Figure 18:
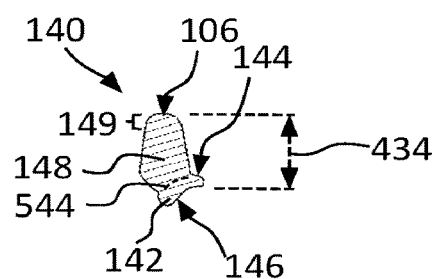
FIG. 18 is a cross-sectional view of the mandibular tray appliance of FIG. 11 taken through section 18-18 of FIG. 16.

Referring to FIG. 18, the second contacting surface (149) is defined as a surface covering a top 2 (two) millimeters of the second contacting portion (148) in successive cross sections. As shown in FIG. 18, the second contacting surface (149) is preferably upwardly converging. The second contacting surface (149) may take any upwardly converging form, such as a rounded form as shown, parabolic form, multi-sided form, chisel shaped form, anteriorly skewed form, posteriorly skewed form, and the like. This upwardly converging form advantageously serves to provide a single point of contact between the second contacting portion (148) and first contacting portion (118) (see FIG. 20A) while allowing for rotational freedom, providing strength against fracture, and/or preventing slipping. The first contacting surface (119) (see FIG. 6) and the second contacting surface (149) (see FIG. 12) are configured to contact each other when a patient bites down with the maxillary tray appliance (110) and the mandibular tray appliance (140) situated in a mouth of the patient.

Throughout this description, the term "upwardly converging" describes a form that is narrower in a top portion than a bottom portion. Conversely, the term "downwardly converging" describes a form that is narrower in a bottom portion than a top portion.

As shown in FIG. 12 and FIG. 18, the second contacting surface (149) of the second contacting portion (148) includes a second ridge line (106).

As shown in FIG. 12, the mandibular tray appliance (140) additionally includes a second longitudinal midline (97). The second ridge line (106) crosses the second longitudinal midline (97) substantially perpendicularly (that is, between 80 degrees and 100 degrees) when viewed from the top. This serves to prevent slipping and/or sliding during contact between the first contacting portion (118) and the second contacting portion (148) (see FIG. 25).

The second ridge line (106) is at least 8 millimeters in length (measured transverse to the second longitudinal midline (97)), and more preferably, the second ridge line (106) is at least 15 millimeters in length. As shown in FIG. 19A, it was determined that if the second ridge line (106) is less than 8 millimeters in length, there would be a high likelihood that the first contacting portion (118) would not be able to contact the second contacting portion (148).

Figure 21:
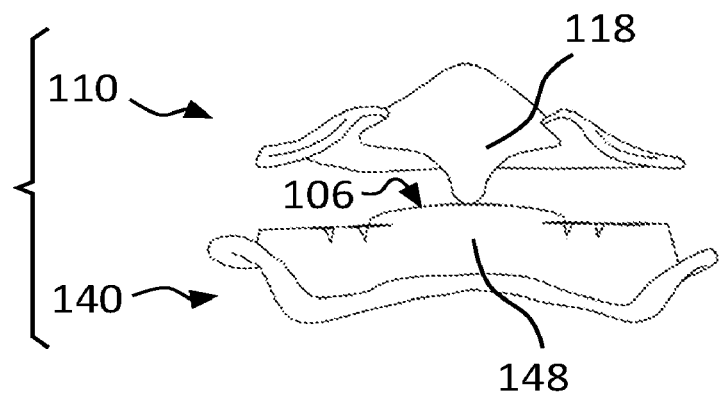
FIG. 21 is a rear view of a tray appliance system showing an upwardly converging second ridge line according to the embodiment of FIG. 19A.
Figure 22:
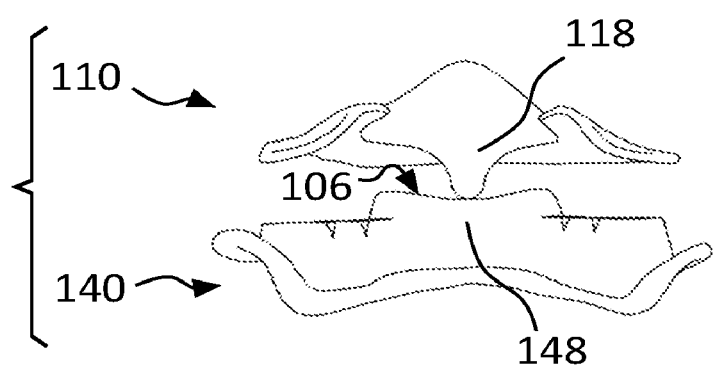
FIG. 22 is a rear view of a tray appliance system showing a downwardly converging second ridge line according to the embodiment of FIG. 19A.

As shown in FIG. 19A, FIG. 21, and FIG. 22, when viewed from the posterior, the second ridge line (106) has a slope of no more than 30 degrees.

Returning to FIG. 6, as previously described, the first ridge line (105) includes the first ridge line midpoint (107), which is defined as an anterior-posterior midpoint of the first ridge line (105).

Since it is not known the precise location of contact between the first contacting portion (118) and the surface originating from the mandibular jaw, it is advantageous for the location of the first ridge line midpoint (107) to be close to an anticipated point of contact (see FIG. 20A).

As shown in FIG. 6 and FIG. 4, the first ridge line midpoint (107) is located anterior to the first transverse midline (103) and is posterior to the first base portion anterior end (131). FIG. 6 does not show the first base portion anterior end (131) because it is obstructed from view by the first contacting portion (118).

It has been determined that if the first ridge line midpoint (107) is located anterior to the first base portion anterior end (131), then the maxillary tray appliance (110) is likely to dislodge anteriorly when the patient bites down. Thus, the first ridge line midpoint (107) being posterior to the first base portion anterior end (131) advantageously serves to prevent dislodgement of the maxillary tray appliance (110) when the patient bites down, which allows an accurate jaw registration to be obtained.

FIG. 20B shows an embodiment in use with a patient's tongue in a "rolled back" position. As shown in FIG. 20B, the size and position of the first ridge line (105) and position of the first ridge line midpoint (107) may serve to encourage the patient to roll the tongue back to a "rolled back" position, and additionally prevents the tongue from posturing forward. The tongue being in a "rolled back" position (instead of posturing forward) advantageously brings the patient's mandible into a centric relation position. The anterior-posterior length of the first ridge line (105) is preferably no more than 60 millimeters. This serves to allow space for the patient's tongue (160) to roll back and/or be in a state of rest without being excessively impinged upon.

If the first ridge line midpoint (107) is posterior to the first transverse midline (103), then the patient's tongue (160) (see FIG. 20B) may not have sufficient room to freely move, such as rolling back, and/or the patient's tongue (160) may be impinged upon by the first contacting portion (118) (see FIG. 20B). Thus, the first ridge line midpoint (107) being anterior to the first transverse midline (103) advantageously serves to provide room for the tongue, which allows an accurate jaw registration to be obtained.

Referring to FIG. 12, the second base portion (142) includes a second transverse midline (104), and the second base portion (142) is divided into equal anterior and posterior portions by the second transverse midline (104) in a top view.

The second ridge line (106) includes a second ridge line midpoint (109), defined as a midpoint in a transverse direction (measured linearly) of the second ridge line (106) in top view. In FIG. 12, the second ridge line midpoint (109) is outlined by a dashed line enclosure. The second ridge line midpoint (109) of the second ridge line (106) is preferably anterior to the second transverse midline (104). This configuration advantageously serves, for example, to provide room for the patient's tongue (160) (see FIG. 20B).

The second ridge line midpoint (109) is preferably posterior to the second base portion anterior end (161). This configuration advantageously serves, for example, to prevent tipping of the mandibular tray appliance (140) when the patient bites down, while providing room for the patient's lower lip.

Returning to FIG. 12, it is preferable but not essential that the second ridge line (106) is anteriorly converging in a top view as shown.). Throughout this description, the term "anteriorly converging" describes a form that is narrower in an anterior portion than a posterior portion.

For example, when the point of contact between the first contacting portion (118) and the second contacting portion (148) is off center (such as to the left), the anteriorly converging form of the second ridge line (106) provides adequate room for the patient's tongue, and prevents the mandibular tray appliance (140) from tipping forward, since the point of contact would be sufficiently posterior to the second base portion anterior end (161) of the second base portion (142) (see FIG. 12). Additionally, as will be described later, when the maxillary tray appliance (110) includes at least one anterior tooth form (132) (see FIG. 28), the anteriorly converging form of the second ridge line (106) prevents contact between the second contacting portion (148) and the anterior tooth form (132).

The second ridge line (106) may also be straight, posteriorly converging, or any other suitable form, such as any anteriorly converging stepped form, anteriorly converging multi-sided form, and the like.

As shown in FIG. 19A, the second ridge line (106) may be substantially straight when viewed in a posterior view. The substantially straight form of the second ridge line (106), when viewed from the posterior, serves to provide the same occlusal vertical dimension regardless of horizontal deviation (of the maxillary tray appliance (110) relative to the mandibular tray appliance (140)). As shown in FIG. 21, the second ridge line (106) may also take an upwardly converging form, which serves to provide a decreased occlusal vertical dimension with increasing horizontal deviation (of the maxillary tray appliance (110) relative to the mandibular tray appliance (140)). In the embodiment shown, preferably, the second ridge line (106) has a bulge height of no more than ten (10) millimeters, and more preferably no more than five (5) millimeters. This embodiment may be advantageous in, for example, patients who have weak joints and would benefit from having a decreased occlusal vertical dimension with increased lateral mandibular deviation. For example, patients having degenerative joint disease, Rheumatoid Arthritis, Ankylosing Spondylitis may benefit from this embodiment.

As shown in FIG. 22, the second ridge line (106) may have a downwardly converging form, which serves to provide more vertical room with increasing horizontal deviation (of the maxillary tray appliance (110) relative to the mandibular tray appliance (140)). This embodiment may be advantageous, for example, in instances where the clinician cannot spend much time obtaining a jaw registration, such as for making a dental prosthesis for a patient prone to gagging. For example, when the maxillary tray appliance (110) and the mandibular tray appliance (140) are horizontally and rotationally deviated from each other, the first contacting portion (118) and the second contacting portion (148) will still be able to contact each other. Additionally, the downwardly converging configuration of the second ridge line (106) discourages the mandible from shifting laterally, and may advantageously be used for patients who are prone to lateral shifting of the mandible. In the embodiment shown, preferably, the second ridge line (106) has a valley depth of no more than ten (10) millimeters and more preferably no more than five (5) millimeters.

As shown in FIG. 24A, the first contacting portion (118) includes a first height (432), which is preferably 3 millimeters to 20 millimeters. The first height (432) is defined as a vertical distance between the first ridge line (105) and the patient's maxillary gum in longitudinal cross section during use. Therefore, when no impression material is being placed on the first top surface (114), the first height (432) may be a least vertical distance between the first top surface (114) and the first ridge line (105). When an impression material is placed on the first top surface (114), the first height (432) may be a least vertical distance between a top surface of the set impression material (not shown) and the first ridge line (105).

The first height (432) serves to provide a suitable distance between the patient's edentulous maxillary jaw and mandibular jaw. A first height (432) of more than 20 mm will usually be too tall, and will provide an occlusal vertical dimension that is too high. A first height (432) of less than 3 mm will usually be too short, and will provide an occlusal vertical dimension that is too low. It is contemplated that in some situations, first height (432) may be more than 20 mm. For example, when the first contacting portion (118) is used to contact mandibular gum, the first height (432) may be between 20 mm and 60 mm. This range serves to provide a suitable occlusal vertical dimension.

As shown in FIG. 18, the second contacting portion (148) includes a second height (434), which is preferably 3 millimeters to 20 millimeters. The second height (434) is defined as a vertical distance between the second ridge line (106) and the patient's mandibular gum in longitudinal cross section during use. Therefore, when no material is being placed on the second bottom surface (146), the second height (434) may be a least vertical distance between the second bottom surface (146) and the second ridge line (106). When an impression material is placed on the second bottom surface (146), the second height (434) may be a least vertical distance between a bottom surface of the set impression material (not shown) and the second ridge line (106). The second height (434) serves to provide a suitable distance between the patient's edentulous maxillary jaw and mandibular jaw. A second height (434) of more than 20 mm will usually be too tall, and will provide an occlusal vertical dimension that is too high. A second height (434) of less than 3 mm will usually be too short, and will provide an occlusal vertical dimension that is too low. The second dashed line (544) indicates a hypothetical location for the second top surface (144) (see FIG. 11) that is integrated into the mandibular tray appliance (140).

Referring to FIG. 24A and FIG. 18, first height (432) and second height (434) may have a combined height (not marked) of, preferably, between 10 (ten) millimeters and 40 (forty) millimeters. This range provides a suitable occlusal vertical dimension for most patients.

Returning to FIG. 24A, the first ridge line (105) of the first contacting surface (119) may be straight in longitudinal cross section. Additionally, when the first ridge line (105) is straight in longitudinal cross section, it is preferred but not essential that the first ridge line (105) be within 20 degrees, and more preferably within 10 degrees of the horizontal plane. This configuration advantageously serves to provide the same occlusal vertical dimension regardless of the patient's jaw relationship (such as, orthognathic, retrognathic, or prognathic, see FIG. 20C and FIG. 20D).

Referring now to FIG. 24B and FIG. 24C, according to some embodiments, at least a portion of the first ridge line (105) may not be straight in longitudinal cross section. For example, as shown in FIG. 24B, the first ridge line (105) may have an arcuate form as shown. Alternatively, for example, as shown in FIG. 24C, the first ridge line (105) may have a multi-sided form as shown. As shown in FIG. 24B and FIG. 24C, for example, an anterior portion (that is, an anterior 20 percent to 70 percent) of the first ridge line (105) may be within 10 degrees to the horizontal plane, while a posterior portion (that is, the remainder of the first ridge line (105)) of the first ridge line (105) may slope upward, for example between 0 degrees and 30 degrees, relative to the anterior portion of the first ridge line (105) when viewed in longitudinal cross section.

The aforementioned embodiments are advantageous in, for example, a situation where it is desirable to have a reduced occlusal vertical dimension in retrognathic jaw configurations. Patients with a retrognathic jaw configuration may have temporomandibular joint(s) that are weaker than patients having orthognathic jaw configurations. Therefore, a decreased occlusal vertical dimension may be advantageous for the health of the patient's joints in a retrognathic jaw configuration. This concept (that is, providing a decreased occlusal vertical dimension to patients that have weak joints) is well known in the field of dentistry, but prior art appliances and/or methods make it difficult and/or time consuming to implement. For example, patients having degenerative joint disease, Rheumatoid Arthritis, Ankylosing Spondylitis may benefit from this embodiment.

Figure 24D:
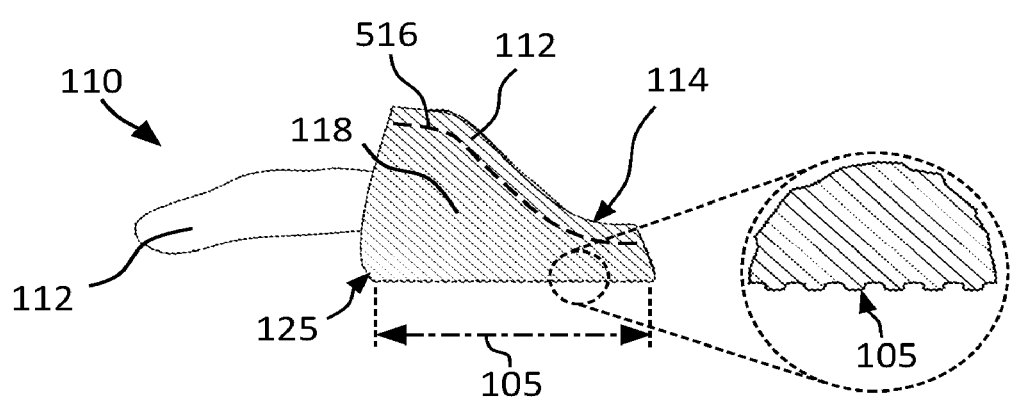
FIG. 24D is a cross-sectional side view and inset view of the maxillary tray appliance of FIG. 1 taken through section 24-24 of FIG. 3, providing an example of a wave-like form of the first ridge line.

Referring now to FIG. 24D, according to an embodiment, the first ridge line (105) may have a wave-like form. For example, in longitudinal cross section, between 10 and 200 ridges may be present. This is shown in the inset view of FIG. 24D. The wave-like form of the first ridge line (105) advantageously prevents anterior or posterior movement of the patient's mandible after the patient bites down. This embodiment is especially advantageous for use in patients who are prone to mandibular jaw movement during setting of bite registration material. Bite registration materials used in dentistry have a setting time of approximately 1 minute to 5 minutes. Therefore, if the patient shifts his/her jaw anteriorly or posteriorly during jaw registration, the resulting jaw registration would be inaccurate. When the patient bites down, the surface originating from the mandibular jaw (such as the second contacting surface (149), see FIG. 18) may be adapted into one of the ridges (see FIG. 24C), thus preventing jaw movement during setting of bite registration material.

It will be understood that when the first ridge line (105) takes a wave-like form (as shown in FIG. 24D), the first ridge line may have a slope of more than 30 degrees in some portions, but a line connecting bottom most points of each of the ridges preferably does not have a slope of more than 30 degrees to the horizontal plane.

Similarly, the second ridge line (106) (see FIG. 19A) may also have a wave-like form (not shown). It will be understood that when the second ridge line (106) takes a wave-like form, the second ridge line may have a slope of more than 30 degrees in some portions, but a line connecting bottom most points of each of the ridges preferably does not have a slope of more than 30 degrees to the horizontal plane.

The forgoing instances of "wave-like form" may be any form having between 10 to 200 ridges, such as, for example, a saw like form, a plurality of block like form, jagged form, and the like.

Returning to FIG. 24D, the wave-like form of the first ridge line (105) may take a straight path as shown, or an arcuate, stepped, or multi-sided path.

As shown in FIG. 27 and FIG. 28, the maxillary tray appliance (110) may include a first occlusal extending portion (122), at least a portion of which downwardly extends from a premolar to molar area of the first base portion (112). Similarly, as shown in FIG. 11 and FIG. 12, the mandibular tray appliance (140) may include a second occlusal extending portion (152), at least a portion of which upwardly extends from a premolar to molar area the second base portion (142) as shown in FIG. 15.

Bite registration materials (or simply "bite materials") are well known in the art, and any bite registration material may be used in combination with any of the various embodiments. Throughout this description, "bite registration material" may be any bite registration material known in the art, such as a silicone material, a polyether material, a polysulfide material, a light cured material, a wax, dental compound, and/or a self-cured material and/or any combinations thereof and the like.

Although, as shown in FIG. 11 and FIG. 12, the second occlusal extending portion (152) and the second contacting portion (148) are shown to be in contact with each other, they may also not be in contact with each other.

An anti-slip element (124) may be included on the second occlusal extending portion (152) (see FIG. 12). The anti-slip element (124) may be in the form of an inwardly extending notch or an outwardly extending geometric shape. As shown in FIG. 28, the anti-slip element (124) may also be included on the first occlusal extending portion (122). In some embodiments, the anti-slip element (124) may be included on the first base portion (112) of the maxillary tray appliance (110) and/or the second base portion (142) of the mandibular tray appliance (140) (not shown).

Figure 31:
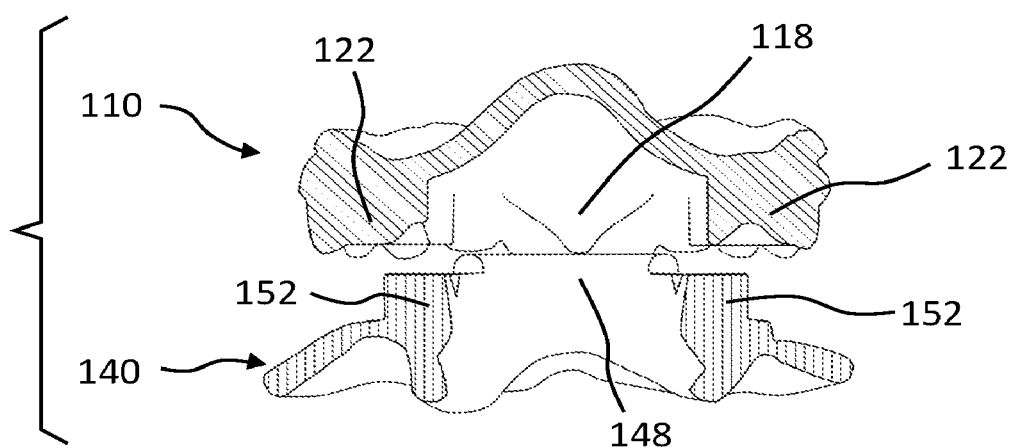
FIG. 31 is a cross-sectional view of the tray appliance of FIG. 25 taken through section line 31-31 of FIG. 26.

As shown in FIG. 25 and FIG. 31, the first occlusal extending portion (122), and/or the second occlusal extending portion (152) may have a block like form as shown, or any other suitable form, such as, for example, a cylindrical form, a plurality of cylindrical form, a multi-sided form, and the like. It is preferable but not essential that at least 80% of a bottom surface of the first occlusal extending portion (122) is flat. Similarly, it is preferable but not essential that at least 80% of a top surface of the second occlusal extending portion (152) is flat. This serves to provide vertical support to bite registration material while providing rotational and/or translational freedom. However, it is contemplated that the bottom surface of first occlusal extending portion (122) and/or the top surface of the second occlusal extending portion (152) may have other configurations, such as a multi-faced surface, a multi-lobular surface, and the like.

Preferably, the first occlusal extending portion (122) has a height (measured vertically from the patient's gum in use) of between 3 mm and 20 mm. Preferably, the second occlusal extending portion (152) has a height (measured vertically from the patient's gum in use) of between 3 mm and 30 mm.

These configurations for the first occlusal extending portion (122) and the second occlusal extending portion (152), respectively, advantageously serve to provide room for the tongue while minimizing the distance between the maxillary tray appliance (110) and the mandibular tray appliance (140). Additionally, when a bite registration material is to be used, the configurations for the first occlusal extending portion (122) and the second occlusal extending portion (152) serves to provide stability to the tray appliance system.

Figure 16:
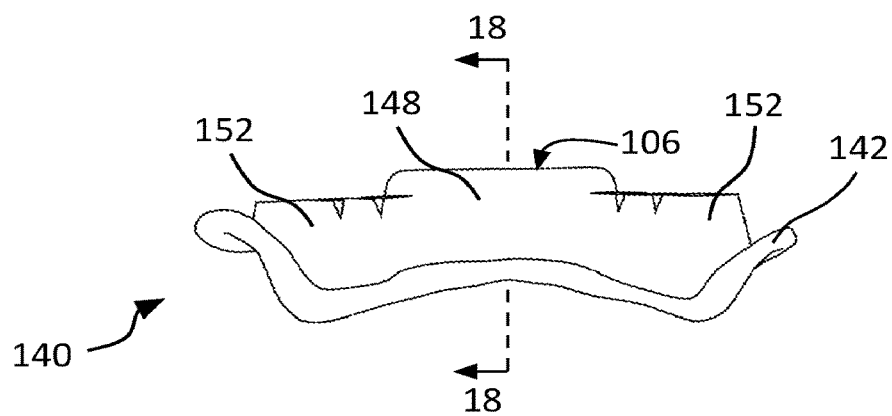
FIG. 16 is a rear view of the mandibular tray appliance of FIG. 11.

As shown in FIG. 16, it is preferable but not essential that a top end of the second ridge line (106) is between 1 millimeter and 10 millimeters taller than a top end of the second occlusal extending portion (152), serving to provide increased rotational freedom.

During use, the clinician may push down on the lateral aspect of the mandibular tray appliance (140), for example, in a premolar to molar area of the mandibular tray appliance (140) to further prevent tipping and/or slipping of the mandibular tray appliance (140).

As shown in FIG. 3, in some embodiments, the first occlusal extending portion (122) may not be present in the maxillary tray appliance (110). This configuration advantageously serves, for example, to allow for more rotational freedom between the maxillary tray appliance (110) and the mandibular tray appliance (140) (see FIG. 19B) and/or between the maxillary tray appliance (110) and mandibular natural teeth (not shown). Similarly, the second occlusal extending portion (152) may not be present on the mandibular tray appliance (140) (not shown).

Referring to FIG. 27, during use, bite registration material may be placed below the first occlusal extending portion (122). After the bite registration material has been placed, the patient may be instructed to bite into the bite registration material. In the embodiment shown in FIG. 25, the mandibular tray appliance (140) may be used. The bite registration material may be placed between the first occlusal extending portion (122) of the maxillary tray appliance (110) and the second occlusal extending portion (152) of the mandibular tray appliance (140). As shown in FIG. 3, in some embodiments, the first occlusal extending portion (122) may not be included in the maxillary tray appliance (110). In use, bite registration material may be placed between the first bottom surface (116) of the first base portion (112) and the second occlusal extending portion (152) (see FIG. 19A). In some embodiments, the second occlusal extending portion (152) may not be included in the mandibular tray appliance (140) (not shown). Thus, bite registration material may be placed between the first bottom surface (116) of the first base portion (112) and the second top surface (144) of the second base portion (142) (not shown). As previously described, the maxillary tray appliance (110) may also be used without the mandibular tray appliance (140). For example, as shown in FIG. 27, bite registration material may be placed between the first occlusal extending portion (122) and the patient's mandibular teeth. For example, bite registration material may be placed between the first occlusal extending portion (122) and the patient's mandibular gum.

Additionally, a bite registration material need not be used. For example, as shown in FIG. 25, the clinician may push down on the mandibular tray appliance (140) using, for example, finger pressure, while capturing a digital scan of the maxillary tray appliance (110) and mandibular tray appliance (140) in the mouth. Finger pressure may be exerted on the mandibular tray by either the clinician, or the patient, or a dental assistant. The digital scan may be obtained using any digitizing device, such as, for example, a laser scanner, an optical scanner, a Cone Beam Computer Tomography machine, a Computer Tomography machine, a Magnetic Resonance Imaging machine, an ultrasonic digitizer, and the like. Bite registration material may also be used. As shown in FIG. 31, bite registration material may be placed between the first occlusal extending portion (122) and the second occlusal extending portion (152), and capturing a digital scan. Following these procedures, a dental prosthesis may be made using any known processes, and/or clinical assessment(s), such as planning for dental implant(s) may be conducted.

FIG. 25 illustrates one preferred embodiment. As shown, the maxillary tray appliance (110) may include a tooth form (130). Including at least one of the tooth form (130) is preferred, but not essential. For example, the tooth form (130) may include an anterior tooth form (132) and/or a posterior tooth form (134). As is commonly defined in dentistry, the term "anterior tooth" may indicate a central incisor tooth, lateral incisor tooth, or canine tooth. Similarly, the term "posterior tooth" may indicate a first premolar tooth, a second premolar tooth, a first molar tooth, a second molar tooth, or a third molar tooth. The maxillary tray appliance (110) may also include a gum portion (136).

The tooth form (130) may extend generally downwardly from a lateral aspect of the first base portion (112). Further, the tooth form (130) may have the form of only a portion of a corresponding tooth. As shown in FIG. 28, for example, the tooth form (130) may have only a facial surface which is substantially similar in form to a corresponding tooth while a lingual surface may have a smooth contour. The form of the lingual surface is not particularly limited.

Figure 32:
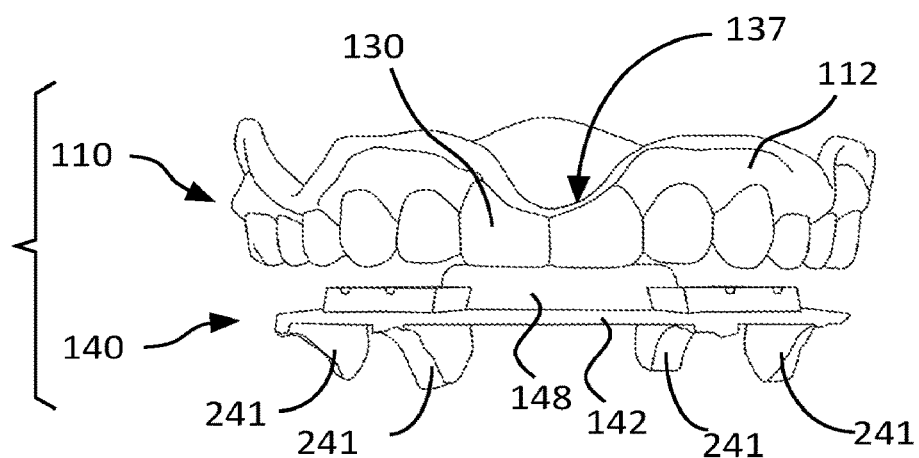
FIG. 32 is an anterior view of an embodiment of the inventive tray system showing a maxillary tray appliance and a mandibular tray appliance.

Additionally, the tooth form (130) may include only a portion of a facial surface of a corresponding tooth, for example, at least 20% of a facial contour of a corresponding tooth. As shown in FIG. 32, the first base portion (112) of the maxillary tray appliance (110) may include contours to accommodate for patient anatomy. For example, the first base portion (112) may include a base portion notch (137) to provide space between the first base portion (112) and patient anatomy, for example, a frenum.

Returning to FIG. 25, in use, the tooth form (130) may be in a position substantially similar to an optimal position of a corresponding tooth. That is, when the maxillary tray appliance (110) is positioned in the patient's mouth, the tooth form (130) may be in a position substantially similar to an optimal position of a corresponding tooth. This position may be determined using any method, such as utilizing a Hamular Notch-Incisive Papilla plane, and/or determining a likely relative position of the first top surface (114) and the patient's maxillary gum by determining a likely impression material thickness. For example, a thickness of silicone impression material may be 0.5 millimeters to 5 millimeters, depending on amount of impression material to be used. This thickness, having been determined, may allow for determination of an optimal positioning of the tooth form (130) on the maxillary tray appliance (110) based on any method, such as utilizing a Hamular Notch-Incisive Papilla plane. The optimal location of the maxillary central incisors is typically approximately 10 millimeters anterior to and 10 millimeters below the patient's incisive papilla, and the patient's occlusal plane is usually substantially parallel with the Hamular Notch-Incisive Papilla plane.

The tooth form (130) having at least 20% of a facial contour of a corresponding tooth advantageously serves to allow the clinician and the patient to visualize a position of teeth in the patient's mouth.

Referring to FIG. 28, when viewed in a bottom view, the posterior tooth form (134) may include a buccal portion of a corresponding posterior tooth. More specifically, for example, when viewed from a bottom view, the posterior tooth form (134) may, for example, include only a buccal 20% to 50% of a corresponding posterior tooth.

Figure 29:
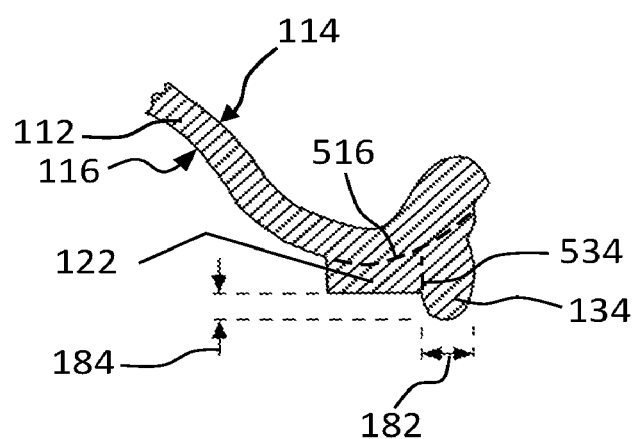
FIG. 29 is a cross sectional view of the maxillary tray appliance of FIG. 25 taken through section line 29-29 of FIG. 28.

The cross-sectional view of FIG. 29 shows an exemplary embodiment in which the posterior tooth form (134) is shown to have a tooth form width (182). The tooth form width (182) indicates a measurement of the posterior tooth form (134) in a buccal-lingual direction. This width may be 20% to 50% of a corresponding tooth. For example, a typical maxillary first premolar denture tooth, such as supplied by a manufacture of denture teeth, such as BLUELINE (manufactured by IVOCLAR of Schaan, Lichtenstein), may have a width of about 10 mm. The posterior tooth form (134) corresponding thereto may have a width of, for example, 2 millimeters to 5 millimeters.

In FIG. 29, a third dashed line (534) indicates a hypothetical junction between the posterior tooth form (134) and the first occlusal extending portion (122). When the first occlusal extending portion (122) and the posterior tooth form (134) contact each other as shown, the posterior tooth form (134) is defined as a portion of the maxillary tray appliance (110) downwardly extending from the first base portion (112) having substantially the same contour as a form of at least a portion of a tooth, while the first occlusal extending portion (122) is defined as a portion of the maxillary tray appliance (110) downwardly extending from the first base portion (112), at least a portion of which is in a premolar to molar area, having a geometric shape that is dissimilar to a tooth.

When the tooth form width (182) is than 50% of a corresponding tooth, the maxillary tray appliance (110) includes a tooth form offset (184). When a first occlusal extending portion (122) is present, the tooth form offset (184) is defined as a vertical offset between a lowest point of the occlusal extending portion and a lowest point of the posterior tooth form (134). The tooth form offset (184) may be, for example, one (1) millimeter to fifteen (15) millimeters. This advantageously serves to allow additional vertical room for the surface originating from the mandibular jaw, such as, a top surface of the second occlusal extending portion (152) (see FIG. 31), while appearing to have a form of a corresponding posterior tooth in a facial aspect (see FIG. 25).

Additionally, as best seen in FIG. 28, in some embodiments, the posterior tooth form (134) may include facial morphology and occlusal morphology of a corresponding tooth. In some embodiments, the posterior tooth form (134) may include only facial morphology of a corresponding tooth. That is, the posterior tooth form (134) may appear in a frontal view to have the appearance of a corresponding posterior tooth, but when viewed from the bottom (as shown in FIG. 28), the posterior tooth form (134) may appear to not have any occlusal morphology (not shown). For example, the posterior tooth form (134) may be substantially smooth in a lingual aspect (not shown).

It will be understood that tooth form offset (184) is preferable but not essential. That is, the anterior tooth form (132) and/or the posterior tooth form (134) may also have a full buccal-lingual contour of a corresponding tooth.

Returning to FIG. 28 and FIG. 29, although the posterior tooth form (134) is shown to be integral with the first bottom surface (116) of the first base portion (112). However, it is contemplated that tooth form (130), which may include the anterior tooth form (132) and/or the posterior tooth form (134) may also take other configurations.

For example, the tooth form (130) may be formed as a separate element from first base portion (112), such as, for example, a removable piece (not shown) which includes one or more tooth form (130), first contacting portion (118), one or more first occlusal extending portion (122). The removable piece may be configured to removably attach to the first base portion (112), using for example, a hub and corresponding receptacle, a snap fit element, a screw, a clip, a plurality of posts and corresponding receptacles, wax, a light cured material, a glue, or the like.

Additionally, the removable piece may be manufactured in any manner in relationship to the first base portion and is not limited by spatial or temporal limitations. For example, the first base portion (112) may be custom manufactured, such as by 3D printing, or using a light cured material, to fit an edentulous individual's oral anatomy, while removable piece (not shown) may be manufactured in bulk. Conversely, the first base portion (112) may be manufactured in bulk, while a plurality of removable pieces, each having different configurations in order for the clinician to have a range of configurations to choose from may be made available to the clinician. For example, the anterior tooth form (132), the first contacting portion (118), and/or the first occlusal extending portion (122) may all be part of an integral piece, and manufactured to have small, medium, and large sizes. The clinician may then choose a size, and attach the manufactured piece to the first base portion (112) that is contoured to individually fit a specific patient. The aforementioned pieces may be attached using any method, such as using wax, a light cured material, a hub and receptacle assembly, and the like.

As best shown in FIG. 28 and FIG. 30, the maxillary tray appliance (110) may include, for example, fewer tooth form(s) than shown. This configuration may be advantageous in, for example, a situation in which a portion of the patient's edentulous (maxillary) ridge is larger than average. Including fewer tooth form(s) advantageously serves to enable the clinician to visualize a vertical, lateral, and anterior-posterior positioning, and also various rotational positions of a proposed posterior tooth form (134), and will enable the clinician to make necessary adjustments to a final tooth setup in 6 degrees of freedom (X, Y, Z, roll, pitch, and yaw).

In some embodiments, pre-manufactured denture teeth may be utilized for the anterior tooth form (132). For example, the pre-manufactured denture teeth may be attached with wax, or snap fit to the maxillary tray appliance (110). Any method of attachment known in the art may be utilized.

Returning to FIG. 25, in some embodiments, the second contacting portion (148) and/or the second occlusal extending portion (152) may not be integral with the second base portion (142). For example, the second contacting portion (148) and the second occlusal extending portion (152) may be portions of an integral piece, but removably attached to the second base portion (142) using any method, such as using wax, a light cured material, a hub and receptacle assembly, and the like.

Figure 33:
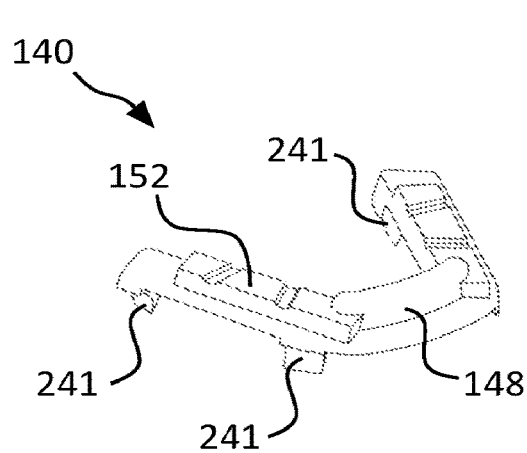
FIG. 33 is a top perspective view of the mandibular tray appliance of FIG. 32.

Referring to FIG. 32, FIG. 33, and FIG. 34, in some embodiments, the mandibular tray appliance (140) may include at least three, and more preferably at least four of the gum contacting portion (241). Referring to FIG. 34, each gum contacting portion (241) includes a gum contacting surface (243), respectively. Each gum contacting surface (243) is configured to make contact with a patient's edentulous gum. Preferably, at least 80 percent (area) of each gum contacting surface (243) is configured to make intimate contact with a patient's mandibular edentulous gum.

Referring to FIG. 32, the gum contacting portion (241) serve to allow the clinician to visualize whether there is intimate contact between the gum contacting surface (243), respectively and the patient's edentulous gum and/or the edentulous gum portion of a dental cast. It is a problem in dentistry that a gum portion of a dental cast, being a replica, does not completely match with the patient's actual oral structure. There may be blebs, bubbles, outward extensions, and/or malformations on the dental cast that is not present in the mouth. For example, these inconsistencies may be formed because of an air bubble in impression material, and/or from the patient's saliva being present during impression taking, and/or from differences in viscosity of impression material (such as difference between impression material used for a preliminary impression versus a final impression). Each gum contacting portion (241) being separated from each other allows the clinician to have unimpeded visualization to see if the gum contacting portion (241) is in intimate contact with the patient's edentulous gum and/or an edentulous gum portion of a dental cast, and allows the clinician to adjust the gum contacting portion (241) as necessary to provide a more intimate contact. Each gum contacting surface (243) is preferably at least 4 (four) millimeters squared (mm^2) in size. Each gum contacting portion (241) is spaced at least 6 (six) millimeters apart, and more preferably at least 10 (ten) millimeters apart. The aforementioned distances are measured between most apical distal ends of each of the gum contacting portion (241), respectively. These configurations provide stability of the mandibular tray appliance (140) and allow for visualization to see if there is intimate contact (see FIG. 30). The previously mentioned "cast" may be a physical cast, such as a cast made of dental stone, or a virtual model, such as a digital representation of a patient's edentulous gum.

In some embodiments, the first base portion (112) of the maxillary tray appliance (110) may include at least one maxillary gum contacting portion (not shown), upwardly extending from the first base portion (112), serving to contact the patient's maxillary gum. When impression material is to be used, the maxillary gum contacting portion advantageously serves to prevent the first base portion (112) from being positioned too close to the maxillary gum during use.

Returning to FIG. 27, the maxillary tray appliance (110) may further include the gum portion (136), which may be formed to have the general contour of natural gums in corresponding areas.

In some embodiments, the gum portion (136) and the tooth form (130) may have different color. For example, the gum portion (136) may be substantially pink while the tooth form (130) may be substantially white. This is advantageous in giving the appearance of the likeness of natural gums and teeth, respectively. This may be accomplished by manual processes or by computer implemented processes. For example, a manual process may include utilizing a pink material, such as pink base plate material (such as a self-cured resin based material, or light-cured material). Additionally, pink wax may be utilized for further enhancement. Alternatively, a computer implemented process may be employed.

For example, a fabricator capable of manufacturing multi-color objects may be utilized. For example, the tooth form (130) may be fabricated in a color substantially similar to natural teeth, such as white, and the gum portion (136) may be fabricated in a color substantially similar to natural gum, such as pink.

This may be done using, for example, a multi-nozzle addition type fabrication device, such as, ULTIMAKER 3 manufactured by ULTIMAKER of Geldermalsen, Netherlands, and the like. Alternative fabrication devices capable of fabricating multi-color objects include SLA-type fabricators, such as OBJET260 CONNEX3 manufactured by STRATASYS of Eden Prairie, Minn. Computer implemented methods for multi-color fabrication are well known in the art, and any known method may be implemented, such as, for example, utilizing a library of virtual tooth forms, and utilizing Boolean subtraction to segment the virtual tooth form from a virtual gum portion.

It will be understood that the aforementioned color "pink" may be any color substantially similar to human gum, such as, for example, light reddish pink, light orange, ethnic pink, or any prosthetic gingival color known in the art. Additionally, the aforementioned color "white" may be any color, gradient, or combination of colors substantially similar to human teeth, such as, for example, A1, A2, A3, B1, B2, B3, etc. shades, gradient shades, or any other dental color, gradient, or combination of colors known in the art.

Yet additionally, colors not found in the human oral cavity may also be used, for example, a blue color, a green color, a gradient color, or any other colors or combination of colors may be used. This serves the purpose of indicating to the patient and/or clinician that the tray appliance(s), such as the mandibular tray appliance (140) is not meant to have similar contours to a dental prosthetic to be fabricated, and serves to avoid confusion. Another example of utilizing a substantially dissimilar color to colors found in the oral cavity may be utilizing the maxillary tray appliance (110), the mandibular tray appliance (140), or any combination(s) thereof for a background in digital merging of images. That is, for example, a green color may be utilized for the maxillary tray appliance (110), and the mandibular tray appliance (140).

A digital photograph may be taken of the patient's smile while the maxillary tray appliance (110) and the mandibular tray appliance (140) are in the mouth. A computing device may be utilized to merge an image of, for example, a digital image of teeth to an area corresponding to the patient's display zone area (area bordered by the patient's lips). This serves the purpose of allowing the patient to visualize different possible tooth set-ups. The aforementioned procedure may also be done in three dimensions, for example, utilizing a 3D camera, such as, for example, REALSENSE camera manufactured by Intel of Santa Clara, Calif. Yet additionally, as mentioned above, lines, curves, grids, or the like, having a different color to surrounding areas may be provided to, for example, at least a facial surface of, for example the maxillary tray appliance (110), for the purpose of aiding alignment of components, such as prosthetic teeth, in subsequent steps.

Any materials suitable for additive manufacturing may be utilized, for example, filament type materials, such as ABS, PLA, photo curable materials, such as DENTAL SG resin (FORMLABS), VERODENT (STRATASYS), metals, such as Co—Cr (such as utilizing an EBM process), and the like. Any materials suitable for subtractive manufacturing may be utilized, for example, any metals, metal alloys, resins, ceramics, and the like.

In some embodiments, at least a portion of the maxillary tray appliance (110) and/or at least a portion of the mandibular tray appliance (140) may include a thickness that may vary by material. For example, as described previously, 3D printed PLA material, which has a tensile strength of about 30 MPa may require more bulk than, for example VERODENT material, which has a tensile strength of about 50-60 MPa, or Co—Cr metal alloy, which has a tensile strength of about 260-840 MPa. Since humans have been found to have bite force of about 400 N, type of material is important in the design of different features.

In some embodiments, at least a portion of the maxillary tray appliance (110) and/or at least a portion of the mandibular tray appliance (140) may be constructed of a thermoplastic material. That is, the at least a portion of the maxillary tray appliance (110) and/or mandibular tray appliance (140) may be constructed of a material that is moldable at a temperature above room temperature, but is substantially rigid at room temperature.

For example, in use, the thermoplastic tray(s) may be warmed in a water bath for at least a portion the tray to achieve a moldable consistency, placing the tray in the mouth or placing the tray on a dental model that is a representation of at least a portion of the mouth, thereby forming the tray to a contour that is more closely adapted to at least a portion of the patient's mouth.

For example, a suitable thermoplastic material may include expanded polystyrene (EPS), a polystyrene derivative, poly(meth)acrylate, a poly(meth)acrylate derivative, polytetrafluoroethylene, polyvinyl fluoride, polychlorotrifluoroethylene, polychlorotrifluoroethylene, polybutadiene, polyisoprene, a derivative of polyisoprene, polyurethane, a derivative of polyurethane or an ethylene copolymers, dental compound, wax, and the like.

Referring to FIG. 6, in some embodiments, a combination of materials may be used. For example, the first contacting portion (118) may be made of a material which has a higher melting range, such as plastic, while the first base portion (112) may be made of a material which has a lower melting range, such as a thermoplastic material. This may be accomplished using any known method(s), such as multi-shot injection molding, overmolding, and the like. This serves to enable the base portion to be adapted to the patient's individual anatomy while allowing the first contacting portion (118) to retain its form.

In some embodiments, at least a portion of the maxillary tray appliance (110) and/or at least a portion of the mandibular tray appliance (140) may be constructed of a light cured material. For example, a suitable light cured material may include urethane dimethyacrylate based materials, triethylene glycol dimethacrylate based materials, and the like. For example, the maxillary tray appliance (110) may be custom made on a stone cast of the patient's edentulous anatomy. For example, the first contacting portion (118) may be manufactured in bulk while the first base portion (112) may be made to adapt to the patient's individual anatomy.

In some embodiments, at least a portion of the maxillary tray appliance (110) and/or at least a portion of the mandibular tray appliance (140) may be constructed of a chemically cured material. For example, a suitable chemically cured material may include polymethyl methacrylate, any polyacrylate, any composite resin, and the like.

INDUSTRIAL APPLICABILITY

The invention has application to the dental industry.

What is claimed is:

1. A tray appliance system for obtaining a bite registration for a patient, the tray appliance system comprising a maxillary tray appliance and a mandibular tray appliance,
the maxillary tray appliance comprising:
a first base portion, the first base portion comprising:
a first top surface opposed to a first bottom surface;
a first middle portion being substantially U shaped in a top view; and
a first medial portion being upwardly extending with slope of at least 10 degrees from a medial side of the first middle portion;
a first contacting portion downwardly extending from the first base portion, the first contacting portion comprising a first contacting surface;
the first contacting surface configured with an anterior-posterior length that is at least twice as long as a transverse width in a bottom view; and
the first contacting surface comprising a first ridge line;
the first ridge line having an anterior-posterior length of no less than 10 millimeters; and
the first ridge line comprising a first ridge line midpoint;
the first base portion further comprising:
a first transverse midline in a bottom view; and
a first base portion anterior end;
the first ridge line midpoint being anterior to said first transverse midline in a bottom view;
the first ridge line midpoint being posterior to said first base portion anterior end;
wherein the first contacting portion is configured to make contact with a surface originating from a mandibular jaw of the patient when the patient bites down;
the mandibular tray appliance comprising:
a second base portion;
the second base portion being U shaped in a bottom view; and
the second base portion comprising a second top surface opposed to a second bottom surface;
a second contacting portion extending upwardly from the second base portion, the second contacting portion comprising a second contacting surface configured with a transverse length that is at least twice as long as an anterior-posterior width in a top view;
the second base portion comprising a second longitudinal midline;
the second contacting surface comprising a second ridge line;
the second ridge line crossing the second longitudinal midline at 80 degrees to 100 degrees in a top view; and
wherein the first contacting portion and second contacting portion are configured to contact each other when a patient bites down with the maxillary tray appliance and the mandibular tray appliance situated in a mouth of the patient.

2. The tray appliance system of claim 1, wherein the first base portion comprises a first base portion length between 45 millimeters and 90 millimeters.

3. The tray appliance system of claim 1, wherein the first contacting surface comprises a first contacting surface width of no more than 15 millimeters.

4. The tray appliance system of claim 1, wherein the first contacting surface is downwardly converging in transverse cross sectional view.

5. The tray appliance system of claim 1, wherein the first base portion further comprises a first lateral portion, said first lateral portion being upwardly extending with slope of at least 10 degrees from a lateral side of the first middle portion.

6. The tray appliance system of claim 1, wherein the first ridge line comprises an anterior-posterior length between 15 millimeters and 60 millimeters.

7. The tray appliance system of claim 1, being configured so that a vertical distance between the first ridge line and a maxillary gum of the patient is between 3 millimeters to 20 millimeters.

8. The tray appliance system of claim 1, wherein the maxillary tray appliance further comprises at least one tooth form.

9. The tray appliance system of claim 1, wherein the maxillary tray appliance further comprises at least one first occlusal extending portion; and at least a portion of said first occlusal extending portion being located in a premolar area to a molar area.

10. The tray appliance system of claim 1, wherein the first ridge line is straight in longitudinal cross sectional view.

11. The tray appliance system of claim 1, wherein the first ridge line is arcuate in longitudinal cross sectional view.

12. The tray appliance system of claim 1, wherein the first ridge line is multi-sided in longitudinal cross sectional view.

13. The tray appliance system of claim 1, wherein the first ridge line is wave-like in longitudinal cross sectional view; and the first ridge line comprises between 10 and 200 ridges.

14. The tray appliance system of claim 1, wherein the first base portion defines at least one aperture.

15. The tray appliance system of claim 1, wherein the second base portion comprises a second transverse midline in a top view and a second base portion anterior end;
- the second ridge line comprising a second ridge line midpoint;
- the second ridge line midpoint being anterior to said second transverse midline; and
- the second ridge line midpoint being posterior to said second base portion anterior end.

* * * * *